(12) United States Patent
Kluckner et al.

(10) Patent No.: US 11,386,291 B2
(45) Date of Patent: Jul. 12, 2022

(54) METHODS AND APPARATUS FOR BIO-FLUID SPECIMEN CHARACTERIZATION USING NEURAL NETWORK HAVING REDUCED TRAINING

(71) Applicant: Siemens Healthcare Diagnostics Inc., Tarrytown, NY (US)

(72) Inventors: Stefan Kluckner, Berlin (DE); Yao-Jen Chang, Princeton, NJ (US); Kai Ma, West Windsor, NJ (US); Vivek Singh, Princeton, NJ (US); Terrence Chen, Princeton, NJ (US); Benjamin S. Pollack, Jersey City, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/961,222

(22) PCT Filed: Jan. 8, 2019

(86) PCT No.: PCT/US2019/012774
§ 371 (c)(1),
(2) Date: Jul. 9, 2020

(87) PCT Pub. No.: WO2019/139922
PCT Pub. Date: Jul. 18, 2019

(65) Prior Publication Data
US 2021/0064927 A1    Mar. 4, 2021

Related U.S. Application Data

(60) Provisional application No. 62/615,873, filed on Jan. 10, 2018.

(51) Int. Cl.
*G06K 9/62* (2006.01)
*G06K 9/20* (2006.01)
(Continued)

(52) U.S. Cl.
CPC ......... *G06K 9/6256* (2013.01); *G06K 9/6271* (2013.01); *G06N 3/04* (2013.01);
(Continued)

(58) Field of Classification Search
CPC .. G06K 9/6256; G06K 9/2018; G06K 9/2054; G06K 9/4647; G06K 9/6271;
(Continued)

(56) References Cited

U.S. PATENT DOCUMENTS 7,473,897 B2 *  1/2009  Braendle ............. G01F 23/2927
                                                 250/343
9,322,761 B2    4/2016  Miller
(Continued)

FOREIGN PATENT DOCUMENTS

JP    2015-026287 A    2/2015
JP    2019-511700 A    4/2019
(Continued)

OTHER PUBLICATIONS

Extended EP Search Report dated Feb. 8, 2021 of corresponding European Application No. 19738207.0, 4 Pages.
(Continued)

*Primary Examiner* — Utpal D Shah

(57) ABSTRACT

A method of training a neural network (Convolutional Neural Network-CNN) including reduced graphical annotation input is provided. The training method can be used to train a Testing CNN that can be used for determining Hemolysis (H), Icterus (I), and/or Lipemia (L), or Normal (N) of a serum or plasma portion of a test specimen. The training method includes capturing training images of multiple specimen containers including training specimens, generating region proposals of the serum or plasma portions of the training specimens; and selecting the best matches for the location, size and shape of the region proposals for the
(Continued)

multiple training specimens. The obtained features (network and weights) from the training CNN can be used in a testing CNN. Quality check modules and testing apparatus adapted to carry out the training method, and characterization methods using abounding box regressor are described, as are other aspects.

23 Claims, 9 Drawing Sheets

(51) Int. Cl.
| | |
|---|---|
| G06K 9/46 | (2006.01) |
| G06N 3/04 | (2006.01) |
| G06N 3/08 | (2006.01) |
| G06T 7/00 | (2017.01) |
| G06V 10/22 | (2022.01) |
| G06V 10/143 | (2022.01) |
| G06V 10/50 | (2022.01) |
| G06V 10/58 | (2022.01) |

(52) U.S. Cl.
CPC ............. *G06N 3/08* (2013.01); *G06T 7/0012* (2013.01); *G06V 10/143* (2022.01); *G06V 10/22* (2022.01); *G06V 10/507* (2022.01); G06T 2207/10036 (2013.01); G06T 2207/10144 (2013.01); G06T 2207/20081 (2013.01); G06T 2207/20084 (2013.01); *G06V 10/58* (2022.01); *G06V 2201/03* (2022.01)

(58) Field of Classification Search
CPC ....... G06K 2009/4657; G06K 2209/05; G06N 3/04; G06N 3/08; G06T 7/0012; G06T 2207/10036; G06T 2207/10144; G06T 2207/20081; G06T 2207/20084
See application file for complete search history.

(56) References Cited

U.S. PATENT DOCUMENTS

| | | | |
|---|---|---|---|
| 9,952,241 B2 | 4/2018 | Miller | |
| 10,267,813 B1* | 4/2019 | Bhatia | G01N 15/05 |
| 10,311,569 B1* | 6/2019 | Bhatia | G06T 7/12 |
| 10,648,905 B2* | 5/2020 | Fritchie | G01N 21/00 |
| 10,713,815 B1* | 7/2020 | Kim | G06K 9/4628 |
| 10,746,665 B2 | 8/2020 | Kluckner et al. | |
| 10,746,753 B2 | 8/2020 | Kluckner et al. | |
| 10,816,538 B2 | 10/2020 | Kluckner et al. | |
| 10,824,832 B2 | 11/2020 | Kluckner et al. | |
| 11,009,467 B2 | 5/2021 | Park et al. | |
| 11,022,620 B2 | 6/2021 | Kluckner et al. | |
| 11,035,870 B2 | 6/2021 | Kluckner et al. | |
| 11,042,788 B2 | 6/2021 | Kluckner et al. | |
| 11,238,318 B2 | 2/2022 | Sun et al. | |
| 2005/0202404 A1 | 9/2005 | Wiltenberg et al. | |
| 2008/0020481 A1* | 1/2008 | Yamamoto | G01N 33/86 436/164 |
| 2012/0140230 A1* | 6/2012 | Miller | G01F 23/292 356/441 |
| 2013/0301901 A1 | 11/2013 | Satish et al. | |
| 2014/0126788 A1* | 5/2014 | Satish | G06T 7/0012 382/128 |
| 2015/0241457 A1* | 8/2015 | Miller | G06K 7/1092 348/143 |
| 2016/0109350 A1* | 4/2016 | Esaki | G01N 33/491 356/39 |
| 2017/0124415 A1 | 5/2017 | Choi et al. | |
| 2017/0169567 A1 | 6/2017 | Chefd'hotel et al. | |
| 2018/0372715 A1 | 12/2018 | Kluckner et al. | |
| 2019/0033209 A1 | 1/2019 | Kluckner et al. | |
| 2019/0073553 A1* | 3/2019 | Yao | G06N 3/08 |
| 2019/0188525 A1* | 6/2019 | Choi | G06K 9/6232 |
| 2019/0383793 A1* | 12/2019 | Sugiyama | G01N 35/00 |
| 2020/0151498 A1 | 5/2020 | Sun et al. | |
| 2020/0151878 A1 | 5/2020 | Kluckner et al. | |
| 2020/0158745 A1 | 5/2020 | Tian et al. | |
| 2020/0265263 A1 | 8/2020 | Kluckner et al. | |

FOREIGN PATENT DOCUMENTS

| | | |
|---|---|---|
| WO | 2009/032315 A1 | 3/2009 |
| WO | 2016/133900 A1 | 8/2016 |
| WO | 2016/144341 A1 | 9/2016 |
| WO | 2017/132166 A1 | 8/2017 |
| WO | 2017/132168 A1 | 8/2017 |

OTHER PUBLICATIONS

Shaoqing Ren et al: "Faster R-CNN: Towards Real-Time Object Detection with Region Proposal Networks", IEEE Transactions on Pattern Analysis and Machine Intelligence, vol. 39, No. 6, Jun. 5, 2016, pp. 1137-1149, XP055705510, USA ISSN: 0162-8828, DOI: 10.1109/TPAMI.2016.2577031.

PCT International Search Report and Written Opinion dated Apr. 9, 2019 (9 Pages).

Paul E. Debevec and Jitendra Malik, "Recovering High Dynamic Range Radiance Maps from Photographs", Proceedings of the 24th annual conference on Computer graphics and interactive techniques (SIGGRAPH '97).

Alex Krizhevsky, Ilya Sutskever, and Geoffrey E. Hinton, "ImageNet Classification with Deep Convolutional Neural Networks", NIPS 2012, pp. 1-9.

Jonathan Long, Evan Shelhamer, and Trevor Darrell, "Fully Convolutional Networks for Semantic Segmentation", CVPR 2015, pp. 3431-3440.

Philipp Krahenbuhl and Vladlen Koltun, "Efficient Inference in Fully Connected CRFs with Gaussian Edge Potentials", NIPS 2011, pp. 1-9.

Anna Khoreva et al., Simple Does It: Weakly Supervised Instance and Semantic Segmentation, pp. 1-21, arXiv:1603.07485v2 [cs.CV] Nov. 23, 2016.

* cited by examiner

METHODS AND APPARATUS FOR BIO-FLUID SPECIMEN CHARACTERIZATION USING NEURAL NETWORK HAVING REDUCED TRAINING

CROSS-REFERENCE TO RELATED APPLICATIONS

This application claims priority to U.S. Provisional Application Ser. No. 62/615,873 filed on Jan. 10, 2018, the contents of which is incorporated herein by reference in its entirety.

FIELD

The present disclosure relates to methods and apparatus for training a neural network to characterize bio-fluid specimens, and, more particularly to methods and apparatus including neural networks for determining if a bio-fluid specimen includes an interferent.

BACKGROUND

Automated testing systems may be used to conduct clinical chemistry or assay testing using one or more reagents to identify an analyte or other constituent in a specimen such as blood serum, blood plasma, or the like. For convenience and safety reasons, these specimens may be contained within specimen containers (e.g., blood collection tubes). In the case where the specimen is whole blood, a gel separator may be added to the specimen container to aid in maintaining separation of a settled blood portion from a serum or plasma portion during centrifugation. The assay or test reactions generate various changes that can be read and/or manipulated to determine the concentration of an analyte or other constituent that is present in the specimen.

Improvements in automated testing technology have been accompanied by corresponding advances in pre-analytical specimen preparation and handling operations such as sorting, batch preparation, centrifuging of specimen containers to separate specimen constituents, cap removal to facilitate specimen access, aliquot preparation, and pre-screening for HILN by automated systems (hereinafter "pre-analytical operations") that may be part of a Laboratory Automation System (LAS). The LAS may automatically transport specimens in the specimen containers to one or more pre-analytical specimen processing stations as well as to analyzer stations containing clinical chemistry analyzers and/or assay instruments (hereinafter collectively "analyzers").

Such specimen containers may have one or more labels provided thereon. The label(s) may be a manufacturer's label and/or a label provided by the phlebotomist or other location or facility handling the specimen. In most instances, at least one label includes identifying information, such as a barcode (hereinafter a "barcode label"). The label(s) may be made of paper with adhesive backing, for example.

The LAS may handle a large number of different specimens at one time, and may use the barcode label for tracking and routing. The barcode label may contain an accession number that may be correlated to demographic information that may be entered into a hospital's Laboratory Information System (LIS) along with test orders and/or other information, wherein the LIS is configured to electronically interface with the LAS. An operator or robot may place the labeled specimen containers onto the LAS system, which automatically routes the specimen containers for one or more pre-analytical operations; all of which may be prior to the specimen actually being subjected to clinical analysis or assaying by one or more analyzers that may be located on a part of the LAS.

After fractionation and other pre-analytical operations, the specimen container may be transported to an appropriate analyzer that may extract, via aspiration, a serum or plasma portion from the specimen container and combine the portion with one or more reagents in a reaction vessel (e.g., cuvette). Analytical measurements may then be performed, often using a beam of interrogating radiation, for example, or by using photometric or fluorometric absorption readings, or the like. The analytical measurements allow determination of end-point or rate values, from which a concentration of the analyte or other constituent may be determined using well-known techniques.

Unfortunately, the presence of any interferent (e.g., H, I, and/or L) in the specimen, as a result of a patient condition or specimen processing, may possibly adversely affect test results of the analyte or constituent measurement obtained from the one or more analyzers. For example, the presence of hemolysis in a blood specimen, which may be unrelated to the patient disease state, may cause a different interpretation of the disease condition of the patient. Moreover, the presence of icterus and/or lipemia in a blood specimen may also cause a different interpretation of the disease condition of the patient. Thus, it is desirable to know via pre-analytical operations, prior to analytical testing, whether a specimen includes H, I, and/or L, and even the index level thereof.

In regards to whether a specimen includes H, I, and/or L, a normal (N) serum or plasma portion has a light yellow to light amber color. Serum or plasma portion containing hemolysis (H) has a reddish color. Serum or plasma portion containing icterus (I) has a dark yellow color due to increased bilirubin, and serum or plasma portion containing lipemia (L) has a whitish or milky appearance. Depending on the color determined by the pre-analytical operations, an interferent type and an index value can be assigned.

In some instances, one or more of the above-described barcode labels may partially occlude and obscure certain lateral viewpoints of the specimen, so that there may be some orientations that do not provide a clear opportunity to visually observe the serum or plasma portion. Thus, automation of such pre-screening has included, for example, rotationally orienting the specimen in such a way that allows for automated pre-screening for H, I, and/or L or N. For example, in some systems, such as those described in U.S. Pat. No. 9,322,761 to Miller entitled "Methods And Apparatus For Ascertaining Interferents And Physical Dimensions in Liquid Samples And Containers To Be Analyzed By A Clinical Analyzer" the specimen container is rotated to find a view window that is unobstructed by the label after which the imaging is carried out.

In other systems, such as those described in WO2016/133900 to Park et al., the specimen container and specimen are imaged from multiple viewpoints and processed with a model-based system so that rotation of the specimen container is not needed. However, in such model-based systems, the upfront training of the model is extremely labor intensive.

Accordingly, there is an unmet need for robust and efficient methods and apparatus adapted to characterize the presence of an interferent in a bio-fluid specimen, and that are able to be trained more efficiently.

SUMMARY

According to a first aspect, a method of training a neural network is provided. The method of training a neural network includes capturing training images of a specimen container containing training specimens at an imaging location, generating region proposals of a serum or plasma portion for input to the neural network, and selecting region proposals that provide best matches for serum or plasma portions of the training specimens.

In another aspect, a method of characterizing a specimen using a trained neural network is provided. The method includes capturing images of a specimen container containing the specimen at an imaging location, generating a region proposal of a serum or plasma portion for input to the neural network, and converging the region proposal through regression to provide a validated region.

According to another aspect, a quality check module configured to determine presence of an interferent in a specimen contained within a specimen container is provided. The quality check module includes an image capture device configured to capture multiple images of a specimen container containing a serum or plasma portion of a specimen, and a computer coupled to the image capture device, the computer configured and capable of being operated to: input image data from the multiple images to a neural network, generate a region proposal of serum or plasma portion, converge the region proposal through regression, and output from the neural network a classification of the serum or plasma portion as being one or more of hemolytic, icteric, lipemic, and normal.

Still other aspects, features, and advantages of the present disclosure may be readily apparent from the following description by illustrating a number of example embodiments and implementations, including the best mode contemplated for carrying out the present invention. The several details of the different embodiments described herein may be modified in various respects, all without departing from the scope of the present disclosure. The disclosure is intended to cover all modifications, equivalents, and alternatives falling within the scope of the claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

Figure 1:
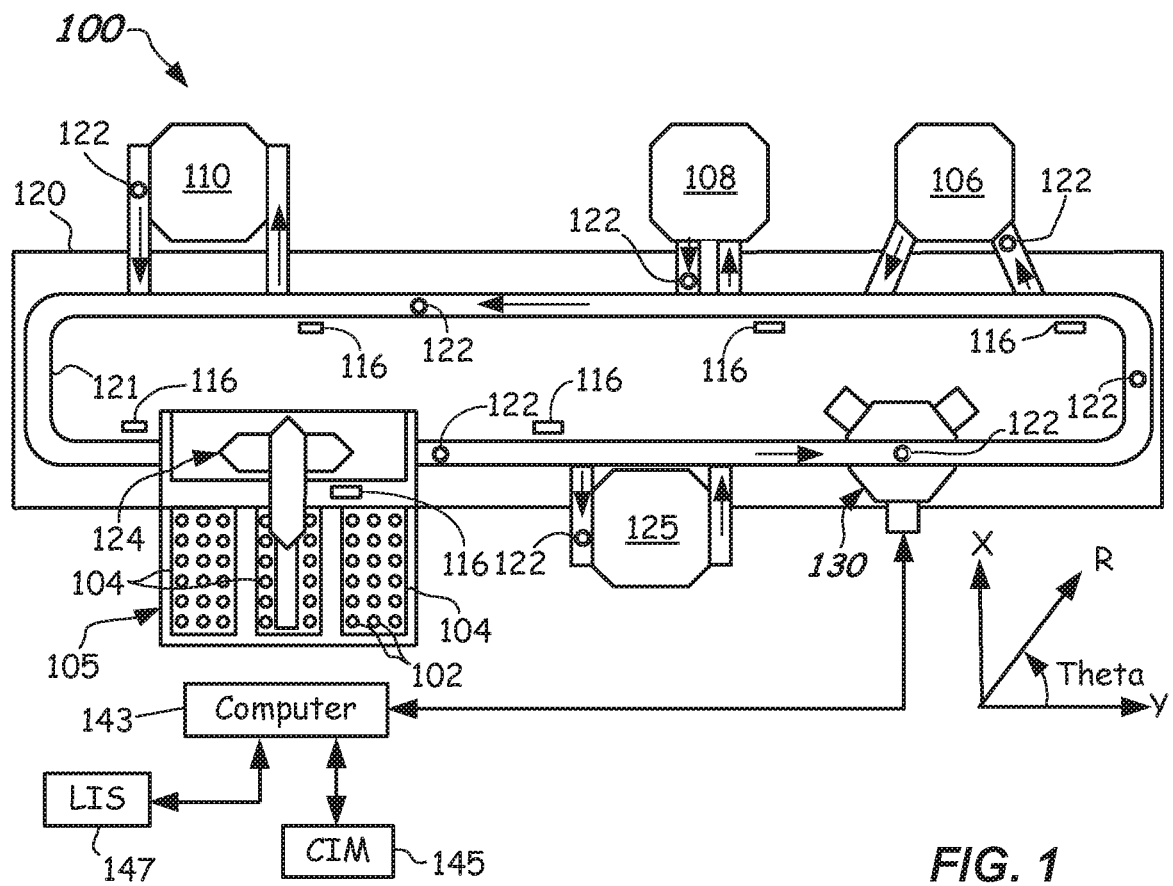
FIG. 1 illustrates a top schematic view of a specimen testing apparatus including one or more quality check modules configured to carry out pre-screening for H, I, and/or L, or N according to one or more embodiments.
Figure 2:
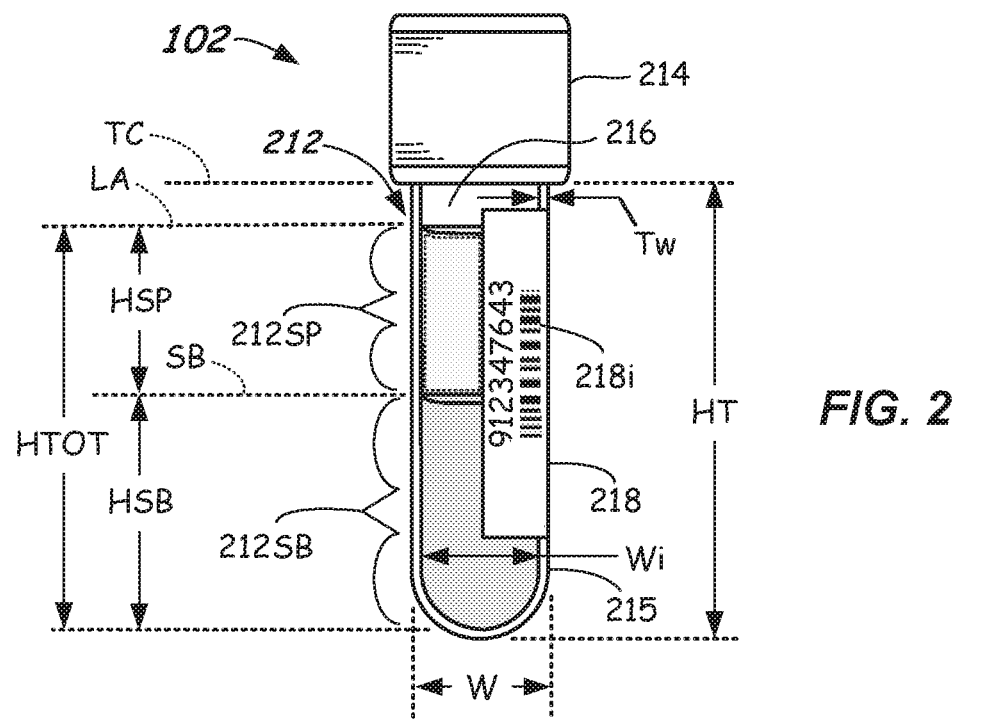
FIG. 2 illustrates a side view of a specimen container including a separated specimen with a serum or plasma portion containing an interferent, and wherein the specimen container includes a barcode label thereon.

Given the above-described deficiencies of methods for training model-based systems for characterizing bio-fluids, methods and apparatus are provided herein that dramatically improve the efficiency of the model training process. In particular, prior art training of model-based systems involves imaging a training specimen having known properties and then an operator would have to manually outline various portions (annotations of graphical regions, such as bounding boxes) within the image of the training specimen. These bounding boxes may outline the peripheral regions of the serum or plasma portion, the settled blood portion, the gel separator, air, and the like. These bounding boxes were provided as the model training annotated input (graphical input) so that the model can be trained to recognize these regions later during specimen testing. Additionally, manual data annotation input may be provided for each manually-generated bounding box such as H, I, L classes or N and/or HIL index values. It should be understood that the provision and input of such manual bounding boxes (of the graphical regions thereof) makes the overall training of the model-based system very cumbersome and extremely time consuming, requiring manual effort by a person. Thus, more efficient model training methods that are less reliant on manual graphical input are greatly needed.

Accordingly, the present disclosure provides methods and apparatus configured to train a model, such as a neural network (e.g., a convolutional neural network-CNN). In particular, the model can be configured and adapted to determine if an interferent is present in a bio-fluid specimen (e.g., HIL) or whether it is normal (e.g., N). The training methods and apparatus described herein are extremely efficient and involve no manual region/graphical annotation input in order to train the neural network (e.g., CNN). Thus, neural network training can be done rapidly and with minimal manual input by an operator.

In a first aspect, the training method involves capturing images of a plurality of specimen containers including training specimens at an imaging location with one or more image capture devices to obtain a plurality of training images (e.g., digital, pixelated training images). Ground truth labels for the model (e.g., Training CNN) are input as training inputs. For each training specimen, interference type and possibly measured or validated index units can be provided as ground truth labels desired as an output from the Testing CNN. Thus, the ground truth labels may be, for example, H, I, and/or L, or N, and/or in other embodiments several discreet index values for each of H, I, and/or L that are desired to be an output from the Testing CNN. The testing CNN is the model once trained and that can then test a specimen for HILN.

Image data pre-processing may be optionally used in some embodiments to accomplish, for example, background removal or tube type detection. Such pre-processing may be used to reduce the size of the image (i.e., to a relevant area of interest), reduce the amount of iterations for convergence, and reduce the overall time for training. To avoid the use of manual graphical input, the methods and apparatus described herein comprise automatic generation of region proposals for the serum or plasma portion. The region proposals that are automatically generated for training, in embodiments, are made up of a sub-region of the imaged area. For example, the sub-region may correspond to a sub-region of a virtual training grid that has been superimposed over the training images. In other words, the region proposals may be a collection of sub-areas of different areas, which are smaller areas within the virtual grid. In embodiments, the virtual training grid may include vertical and horizontal lines intersecting and forming virtual nodes of the virtual grid at the intersections. A collection or grouping of grid elements within the virtual grid may constitute a region proposal.

For example, the region proposals may encompass rectangular sub-regions within the training image. For example, in some embodiments the region proposal may be generated by selecting two virtual nodes (e.g., diagonally-opposing corner nodes) within the virtual grid. A particular region proposal may be selected randomly in some embodiments. Thousands of training images are captured and input to the training CNN and thousands of randomly-generated region proposals are also generated and input to the Training CNN along with ground truth information on HILN and possibly HIL index levels. Each of the various region proposals may be verified for degree of correlation (fit) with the location of the serum/plasma portion within the entered image data.

For example, each region proposal may be tested/verified by filtering, such as by examining light intensity gradients within each of the region proposals. For example, the degree of match may be discriminated by examining gradients of light intensity within certain portions of the training images. Those portions with good correlation may be kept, while those with poor correlation can be discarded. Thus, a plurality of the best proposals (e.g., several thousand) may be selected based upon the degree of "match" with the inputted training images, i.e., those region proposals that have the highest correlation can be used.

In some instances, the virtual grid can be made up of rectangular-shaped grid elements that have a width (W) and height (H) in size. A suitably fine grid should be used, so that a good estimate of the size and shape or the serum or plasma portion can be obtained. Each region proposal is generated (e.g., randomly) and is submitted as an input to the Training CNN along with the training images and ground truth labels and degree of convergence is tested. Convergence means that in 80% of the cases, or even 90%, or even 95%, or higher, the correct result is obtained. If sufficient convergence is obtained during the training, then the training can be stopped. The consideration of proper training can be achieved by consideration of the loss for the HIL classification part (SoftMax).

Once the Training CNN is sufficiently trained, the various features and/or model weights may be transferred and used as part of a Testing CNN configured to automatically recognize the serum or plasma portion of a test specimen in a specimen container and provide a suitable classification as H, I, and/or L or N, and if the model has been trained to do so, an H, I, or L index thereof.

Thus, once trained, the Testing CNN may be used to determine the presence of an interferent, such as H, I, and/or L, or N (hereinafter "HILN") in the serum or plasma portion of the specimen or some HIL subset thereof. The method and neural network (e.g., testing CNN) may be configured to determine n-Class H (e.g., H1, H2, H3, or more), n-Class I (e.g., I1, I2, I3, or more), and/or n-Class L (e.g., L1, L2, L3, or more), or N. In some embodiments, the Testing CNN is capable of identifying all three of n-Class H, and n-Class I, and n-Class L. Notably, although a 10-class Testing CNN is shown, including H with n=3, I with n=3, L with n=3, and N, other numbers of outcomes may be used, such as n=4, 5, 6, 7, 8, or more.

Differentiation of the serum and plasma portion from the region comprising one or more labels is a particularly vexing problem because the one or more labels may wrap around the specimen container to various degrees. Thus, the one or more labels may obscure one or more viewpoints, such that a clear view of the serum or plasma portion may be difficult to obtain. Thus, classification of the serum or plasma portion may be quite challenging due to interference from the one or more labels, whose placement may vary substantially from one specimen container to the next being pre-screened.

In particular, the obstruction caused by the one or more labels may heavily influence the spectral responses, such as from various viewpoints, given that the one or more labels may appear on a back side and thus affect light transmission received at the front side. Given this, the input to the Training CNN may be multi-spectral, multi-exposure image data, which may be pre-processed (e.g., consolidated and normalized), and obtained from more than one image capture device. For example, the image capture devices may comprise multiple image capture devices arranged and configured to capture images from more than one viewpoint (e.g., three lateral viewpoints, for example).

In some embodiments of the training method, some easier training examples (e.g., without labels) may be first trained at various levels of HIL and N and from multiple viewpoints. Then, more difficult training examples including various locations and numbers of labels (e.g., up to two labels) may be input as training specimens at the multiple viewpoints. As a result, more effective training of the Training CNN to recognize the serum or plasma region may be provided in cases where label obstruction is present.

Definitions

"Interferent," as used herein, means the presence of at least one of hemolysis (H), icterus (I), or lipemia (L) in the serum or plasma portion of the specimen. Hemolysis (H), icterus (I), and lipemia (L) are collectively referred to as "HIL" herein.

"Hemolysis" is defined as a condition in the serum or plasma portion wherein during processing red blood cells are destroyed, which leads to the release of hemoglobin from the red blood cells into the serum or plasma portion such that the serum or plasma portion takes on a reddish hue. The degree of Hemolysis (H) may be quantified by assigning a Hemolytic Index.

"Icterus" is defined as a condition of the blood where the serum or plasma portion is discolored dark yellow caused by an accumulation of bile pigment (bilirubin). The degree of Icterus (I) may be quantified by assigning an Icteric Index.

"Lipemia" is defined as a presence in the blood of an abnormally high concentration of emulsified fat, such that the serum or plasma portion includes a whitish or milky appearance. The degree of Lipemia (L) may be quantified by assigning a Lipemic Index.

"Normal" is defined as serum or plasma portion that includes acceptably low amounts of H, I, and L and is designated herein as N.

"Serum or plasma portion" is the liquid component of blood. It is found above the settled blood portion after fractionation (e.g., by centrifugation). Plasma and serum differ in the content of coagulating components, primarily fibrinogen. Plasma is the un-clotted liquid, whereas serum refers to blood plasma, which has been allowed to clot either under the influence of endogenous enzymes or exogenous components.

"Settled blood portion" is a packed semi-solid made up blood cells such as white blood cells (leukocytes), red blood cells (erythrocytes), and platelets (thrombocytes), which are aggregated and separated from the serum or plasma portion. The settled blood portion is found at a bottom part of the specimen container below the serum or plasma portion after fractionation.

"Image capture device" is any device capable of capturing a pixelated image (e.g., digital image) for analysis, such as a digital camera, a CCD (charge-coupled device), a CMOS (complementary metal-oxide semiconductor), an array of sensors or photodetectors, or the like.

"Pixelated image" as used herein means images made up of either single pixels or a grouping of pixels, such as a super-pixel or image patch (patch) including more than one pixel.

"Label" is defined as an area on an outside surface of the specimen container adapted to contain identification information (i.e., indicia). The label may be an opaque paper, plastic, paint, or other material applied to an outer surface of the specimen container. Indicia may be a barcode, alphabetic characters, numeric characters, or combinations thereof. The label may be manufacturer label or may be a label after-applied by a phlebotomist or by a subsequent specimen processing entity and may include a barcode.

"LA" is defined as the liquid-air interface and is a line of demarcation (viewed laterally) between the serum or plasma portion and the air above the serum or plasma portion.

"SB" is the serum-blood interface, which is a line of demarcation (viewed laterally) between the serum or plasma portion and the settled blood portion.

"TC" is the tube-cap interface, which is a line of demarcation (viewed laterally) at the interface between the air and the cap.

"HT" is the height of the tube and is defined as the height from the bottom-most part of the tube to the bottom of the cap.

"HSP," in cases where no gel separator is used, is the height of the serum or plasma portion and is defined as the height from the top of the serum or plasma portion from the top of the settled blood portion, i.e., from LA to SB.

"HSP," in cases where a gel separator is used (FIG. 3A), is a height of the serum or plasma portion and is defined as a height from the top of the serum or plasma portion at LA to the top of the gel separator at SG, i.e., from LA to SG.

"HSB," in cases where no gel separator is used, is the height of the settled blood portion and is defined as the height from the bottom of the settled blood portion to the top of the settled blood portion at SB.

"HSB," in cases where a gel separator is used, is the height of the settled blood portion and is defined as the height from the bottom of the settled blood portion to the bottom of the gel separator at BG.

"HTOT," in cases where there is no gel separator is used, is the total height of the specimen and equals HSP+HSB.

"HTOT," in cases where a gel separator is used, is a total height of the specimen, and equals HSP+HSB+height of the gel separator.

"Tw" is the wall thickness of the specimen container.

"W" is an outer width of the specimen container.

"Wi" is an inner width of the specimen container.

"Carrier" is a device that is configured to support and transport a specimen container, such as within a laboratory automation system (LAS).

"VSP" is a volume of the serum or plasma portion in the specimen container.

"VSB" is a volume of the settled blood portion in the specimen container.

"Hemolytic index" as used herein means a grade given to a particular specimen based upon the determined content (degree or amount) of hemolysis present in the serum or plasma portion.

"Icteric index" as used herein means the grade given to a particular specimen based upon a determined content (degree or amount) of icterus present in the serum or plasma portion.

"Lipemic index" as used herein means the grade given to a serum or plasma portion based upon the determined content (degree or amount) of lipemia present in the serum or plasma portion.

"Convolution" as used herein means a processing step that learns and applies filter kernels. During a forward pass, the filter is applied to the input image data by computing a dot product. This results in an activation map of that filter. Thus, the network learns filters that activate when the processing detects some specific type of feature at some spatial position in the input image data.

"Pooling" as used herein means a processing step that performs non-linear down sampling. Typically, max pooling is applied. Max pooling is achieved by applying a max filter to non-overlapping sub-regions of the representation.

"SoftMax" as used herein is a loss that is used for predicting a single class of N mutually exclusive classes.

The ability to pre-screen for HILN right after centrifugation and before analysis by one or more analyzers may advantageously minimize wasted time analyzing specimens that are not of the proper quality for analysis, may avoid or minimize erroneous test results, may minimize patient test result delay, and may avoid wasting of patient specimen. Moreover, in one or more embodiments, remedial action can take place after pre-screening for HILN wherein unacceptable levels of H, I, and/or L are identified in the serum or plasma portion of the specimen.

The specimen containers provided for training of the model (training CNN) may be of different sizes, including different widths and different heights, and thus may be supplied for training and later pre-screening in a number of different physical configurations. For example, the specimen containers can have sizes such as 13 mm×75 mm, 13 mm×100 mm, 16 mm×100 mm, and 16 mm×125 mm, for example. Other suitable specimen container sizes may be encountered.

The methods described herein can use high dynamic range (HDR) image processing of the specimen container and serum or plasma portion as an input to the Training CNN as well as the Testing CNN. HDR imaging involves capturing multiple exposures, while using multiple spectral illuminations, as will be apparent from the following.

In one or more embodiments, a quality check module may be configured to carry out the training methods and testing methods described herein. The quality check module may be implemented in any suitable area of a LAS, preferably where a robotic mechanism (e.g., a gripper-finger robot) or a track may facilitate transport of specimen containers thereto. In some embodiments, the quality check module may be provided on or along a track of a specimen testing apparatus and a carrier supporting the specimen container may be configured to move the specimen to an imaging location in the quality check module in order to accurately train to discriminate HILN with the image-based quality check module.

However, in some embodiments, training may alternatively take place on a training module at a different location that the testing location of the specimen testing apparatus, wherein the training module is an exact duplicate of the quality check module used for pre-screening. In some implementations, the track may carry the specimens to the pre-screening locations and also to one or more remote locations for analysis (e.g., clinical chemistry testing or assaying) on an analyzer on carriers. In embodiments, the training specimen container may be held in an upright position during training (and testing), such as by a holder. The holder may include fingers or other suitable articles that hold the specimen container in an approximately vertically upright orientation during capture of the respective images. The holder may be part of the carrier in some embodiments.

The training images may be obtained, in some embodiments, by multiple image capture devices located so as to capture training images from multiple viewpoints (e.g., multiple lateral viewpoints). The multiple training images may be obtained at the quality check module, and may be captured at multiple exposures (e.g., exposure times) while providing illumination (e.g., backlighting) at multiple spectra, wherein each spectra has a different nominal wavelength.

The multiple spectra of illumination may include emitted lighting of red (R), green (G), and/or blue (B) light, for example. In other embodiments, white (W), infrared (IR) and/or near IR (NIR), may be used for illumination. Any combination of the afore-mentioned illumination sources may be used. The illumination may include backlit illumination wherein an image capture device is located on one side and the backlight source is on an opposite side of the specimen container. The exposure time may be varied based upon the lighting intensity and spectrum used and features of the image capture device(s). Multiple exposure times (e.g., 4-8 different exposures) may be used for each spectrum and for each image capture device (i.e., for each viewpoint). Other numbers of exposures may be used.

In an image data pre-processing operation, for each corresponding pixel (or patch, if using patch-wise processing) of the multiple captured images at a particular spectrum (at different exposure times), pixels (or patches) exhibiting optimal image intensity may be selected. These selected pixels (or patches) exhibiting optimal image intensity may also be normalized. The result may be a plurality of consolidated and normalized color image data sets, one image data set for each different spectrum of illumination (e.g., R, G, B, W, IR, and/or NIR) and for each viewpoint. These consolidated and normalized data sets may be provided in the form of data matrices as layers to the Training CNN. Once properly trained, images that are taken of each test specimen (test images) can be operated upon by a Testing CNN to determine HILN. In some embodiments, a determination of interference type (HIL) is provided as an output from the Testing CNN. In other embodiments, the output of the Testing CNN can be an n-class HIL or normal (N).

Further details of the inventive training methods and training quality check modules configured to carry out the training methods are further described with reference to FIGS. 1-8 herein.

FIG. 1 illustrates a specimen testing apparatus 100 capable of automatically processing multiple specimen containers 102 (e.g., see FIGS. 2-3B) containing specimens 212. The specimen containers 102 may be provided in one or more racks 104 at a loading area 105 prior to transportation to and analysis by one or more analyzers (e.g., first, second, and third analyzer 106, 108, and/or 110, respectively) arranged about the specimen testing apparatus 100. More or less numbers of analyzers can be used. The analyzers may be any combination of clinical chemistry analyzers and/or assaying instruments, or the like. The specimen containers 102 may be any suitably transparent or translucent container, such as a blood collection tube, test tube, sample cup, cuvette, or other clear or opaque glass or plastic container capable of containing and allowing imaging of the specimen 212 contained therein. The specimen containers 102 may be varied in size as discussed above.

Specimens 212 may be provided to the specimen testing apparatus 100 in the specimen containers 102, which may be capped with a cap 214. The caps 214 may have different cap colors (e.g., red, royal blue, light blue, green, grey, tan, yellow, or color combinations), which can have meaning in terms of what test the specimen container 102 is used for, the type of additive included therein, whether the container includes a gel separator, or the like. Other colors may be used.

Each of the specimen containers 102 may be provided with a label 218, which may include identification information 218$i$ (i.e., indicia) thereon, such as a barcode, alphabetic, numeric, or combination thereof. The identification information 218$i$ may be machine readable at various locations about the specimen testing apparatus 100. The machine readable information may be darker (e.g., black) than the label material (e.g., white) so that it has contrast that can be readily imaged. The identification information 218$i$ may indicate, or may otherwise be correlated, via a Laboratory Information System (LIS) 147, to a patient's identification as well as tests to be accomplished upon the specimen 212, or other information, for example. Such identification information 218$i$ may be provided on the label 218 that may be adhered to or otherwise provided on an outside surface of the tube 215. In the depicted embodiment of FIG. 2, the label 218 may not extend all the way around the specimen container 102, or all along a length of the specimen container 102. Thus, from the particular front viewpoint shown, a large part of the serum or plasma portion 212SP is clearly viewable and is capable of being imaged (the part shown dotted) and is unobstructed by the label 218.

However, in some embodiments, multiple labels 218 may have been provided (such as from multiple facilities that have handled the specimen container 102), and they may overlap each other to some extent. For example, two labels (e.g., a manufacturer's label and a barcode label) may be provided and may be overlapping and may occlude (obstruct) some viewpoints. Thus, it should be understood that in some embodiments, although the label(s) 218 may occlude some portion of the specimen 212 (occluded portion), some portion of the specimen 212 and serum and plasma portion 212SP may still be viewable from at least one viewpoint (un-occluded portion). Thus, in accordance with another aspect of the disclosure, embodiments of the Training CNN configured to carry out the training method can be trained to recognize the occluded and un-occluded portions, such that improved HILN detection may be provided.

Again referring to FIG. 2, the specimen 212 may include the serum or plasma portion 212SP and a settled blood portion 212SB contained within the tube 215. Air 216 may be provided above the serum and plasma portion 212SP and a line of demarcation between them is defined as the liquid-air interface (LA). The line of demarcation between the serum or plasma portion 212SP and the settled blood portion 212SB is defined as a serum-blood interface (SB). An interface between the air 216 and cap 214 is defined as a tube-cap interface (TC). The height of the tube (HT) is defined as a height from a bottom-most part of the tube 215 to a bottom of the cap 214, and may be imaged and used for determining tube height. A height of the serum or plasma portion 212SP is (HSP) and is defined as a height from a top of the serum or plasma portion 212SP from a top of the settled blood portion 212SB. A height of the settled blood portion 212SB is (HSB) and is defined as a height from the bottom of the settled blood portion 212SB to a top of the settled blood portion 212SB at SB. HTOT is a total height of the specimen 212 and equals HSP plus HSB.

In cases where a gel separator 313 is used (FIG. 3A), the height of the serum or plasma portion 212SP is (HSP) and is defined as a height from atop of the serum or plasma portion 212SP at LA to the top of the gel separator 313 at SG, wherein SG is an interface between the serum or plasma portion 212SP and the gel separator 313. A height of the settled blood portion 212SB is (HSB) and is defined as a height from the bottom of the settled blood portion 212SB to the bottom of the gel separator 313 at BG, wherein BG is an interface between the settled blood portion 212SB and the gel separator 313. HTOT is the total height of the specimen 212 and equals HSP plus HSB plus height of the gel separator 313. In each case, Tw is a wall thickness, W is an outer width, which may also be used for determining the size of the specimen container 102, and Wi is an inner width of the specimen container 102.

In more detail, specimen testing apparatus 100 may include a base 120 (e.g., a frame, floor, or other structure) upon which a track 121 may be mounted. The track 121 may be a railed track (e.g., a mono rail ora multiple rail), a collection of conveyor belts, conveyor chains, moveable platforms, or any other suitable type of conveyance mechanism. Track 121 may be circular or any other suitable shape and may be a closed track (e.g., endless track) in some embodiments. Track 121 may, in operation, transport individual ones of the specimen containers 102 to various locations spaced about the track 121 in carriers 122.

Carriers 122 may be passive, non-motored pucks that may be configured to carry a single specimen container 102 on the track 121, or optionally, an automated carrier including an onboard drive motor, such as a linear motor that is programmed to move about the track 121 and stop at pre-programmed locations. Other configurations of carrier 122 may be used. Carriers 122 may each include a holder 122H (FIG. 3B) configured to hold the specimen container 102 in a defined upright position and orientation. The holder 122H may include a plurality of fingers or leaf springs that secure the specimen container 102 on the carrier 122, but some may be moveable or flexible to accommodate different sizes (diameters) of the specimen containers 102. In some embodiments, carriers 122 may leave from the loading area 105 after being offloaded from the one or more racks 104. The loading area 105 may serve a dual function of also allowing reloading of the specimen containers 102 from the carriers 122 to the loading area 105 after pre-screening and/or analysis is completed. Delivery and routing of training specimens may use the same approach.

A robot 124 may be provided at the loading area 105 and may be configured to grasp the specimen containers 102 from the one or more racks 104 and load the specimen containers 102 onto the carriers 122, such as onto an input lane of the track 121. Robot 124 may also be configured to reload specimen containers 102 from the carriers 122 to the one or more racks 104. The robot 124 may include one or more (e.g., least two) robot arms or components capable of X (lateral) and Z (vertical—out of the paper, as shown), Y and Z, X, Y, and Z, or r (radial) and theta (rotational) motion. Robot 124 may be a gantry robot, an articulated robot, an R-theta robot, or other suitable robot wherein the robot 124 may be equipped with robotic gripper fingers oriented, sized, and configured to pick up and place the specimen containers 102.

Upon being loaded onto track 121, the specimen containers 102 carried by carriers 122 may progress to a first pre-processing station 125. For example, the first pre-processing station 125 may be an automated centrifuge configured to carry out fractionation of the specimen 212. Carriers 122 carrying specimen containers 102 may be diverted to the first pre-processing station 125 by inflow lane or other suitable robot. After being centrifuged, the specimen containers 102 may exit on outflow lane, or otherwise be removed from the centrifuge by a robot, and continue along the track 121. In the depicted embodiment, the specimen container 102 in carrier 122 may next be transported to a quality check module 130 to carry out training or pre-screening, as will be further described herein. The degree of HILN for each of the specimens 212 as well as the container size in the racks 105 is known during training and thus can be provided to the Training CNN via correlation with the label 218.

The quality check module 130, once trained, is configured to pre-screen is configured to automatically determine a presence of, and possibly an extent of H, I, and/or L contained in a specimen 212 or whether the specimen is normal (N). If found to contain effectively-low amounts of H, I and/or L, so as to be considered normal (N), the specimen 212 may continue on the track 121 and then may be analyzed by the one or more analyzers (e.g., first, second, and/or third analyzers 106, 108, and/or 110). Thereafter, the specimen container 102 may be returned to the loading area 105 for reloading to the one or more racks 104.

The specimen testing apparatus 100 may include a number of sensors 116 at one or more locations around the track 121. Sensors 116 may be used to detect a location of specimen containers 102 on the track 121 by means of reading the identification information 218$i$, or like information (not shown) provided on each carrier 122. Any suitable means for tracking the location may be used, such as proximity sensors. All of the sensors 116 may interface with the computer 143, so that the location of each specimen container 102 may be known at all times. The sensors 116 may, during training, be used to identify the specimen 212 that has been routed to the quality check module 130 for training.

The pre-processing stations and the analyzers 106, 108, 110 may be equipped with robotic mechanisms and/or inflow lanes configured to remove carriers 122 from the track 121, and robotic mechanisms and/or outflow lanes configured to reenter carriers 122 to the track 121.

Specimen testing apparatus 100 may be controlled by the computer 143, which may be a microprocessor-based central processing unit CPU, having a suitable memory and suitable conditioning electronics and drivers for operating the various system components. Computer 143 may be housed as part of, or separate from, the base 120 of the specimen testing apparatus 100. The computer 143 may operate to control movement of the carriers 122 to and from the loading area 105, motion about the track 121, motion to and from the first pre-processing station 125 as well as operation of the first pre-processing station 125 (e.g., centrifuge), motion to and from the quality check module 130 as well as operation of the quality check module 130, and motion to and from each analyzer 106, 108, 110 as well as operation of each analyzer 106, 108, 110 for carrying out the various types of testing (e.g., assay or clinical chemistry). During training, the computer 143 may be used to accomplish the training of the Training CNN. Optionally, a separate computer may carry out the model training.

For all but the quality check module 130, the computer 143 may control the specimen testing apparatus 100 according to software, firmware, and/or hardware commands or circuits such as those used on the Dimension® clinical chemistry analyzer sold by Siemens Healthcare Diagnostics Inc. of Tarrytown, N.Y., and such control is typical to those skilled in the art of computer-based electromechanical control programming and will not be further described herein. However, other suitable systems for controlling the specimen testing apparatus 100 may be used. The control of the quality check module 130 may also be provided by the computer 143, but according to the methods described in detail herein. In particular, methods and apparatus to accomplish rapid training of the specimen testing apparatus 100 are provided.

The computer 143 used for image processing carried out for the characterization/testing and training methods described herein may include a CPU or GPU, sufficient processing capability and RAM, and suitable storage. In one example, the computer 143 may be a multi-processor-equipped PC with one or more GPUs, 8 GB Ram or more, and a Terabyte or more of storage. In another example, the computer 143 may be a GPU-equipped PC, or optionally a CPU-equipped PC operated in a parallelized mode. MKL could be used as well, 8 GB RAM or more, and suitable storage.

Testing embodiments of the disclosure may be implemented using a computer interface module (CIM) 145 that allows for a user to easily and quickly access a variety of control and status display screens. These control and status display screens may display and enable control of some or all aspects of a plurality of interrelated automated devices used for preparation and analysis of specimens 212. The CIM 145 may be employed to provide information about the operational status of a plurality of interrelated automated devices as well as information describing the location of any specimen 212 as well as a status of tests to be performed on, or being performed on, the specimen 212. The CIM 145 is thus adapted to facilitate interactions between an operator and the specimen testing apparatus 100. The CIM 145 may include a display screen adapted to display a menu including icons, scroll bars, boxes, and buttons through which the operator may interface with the specimen testing apparatus 100. The menu may comprise a number of function elements programmed to display and/or operate functional aspects of the specimen testing apparatus 100.

Figure 4A:
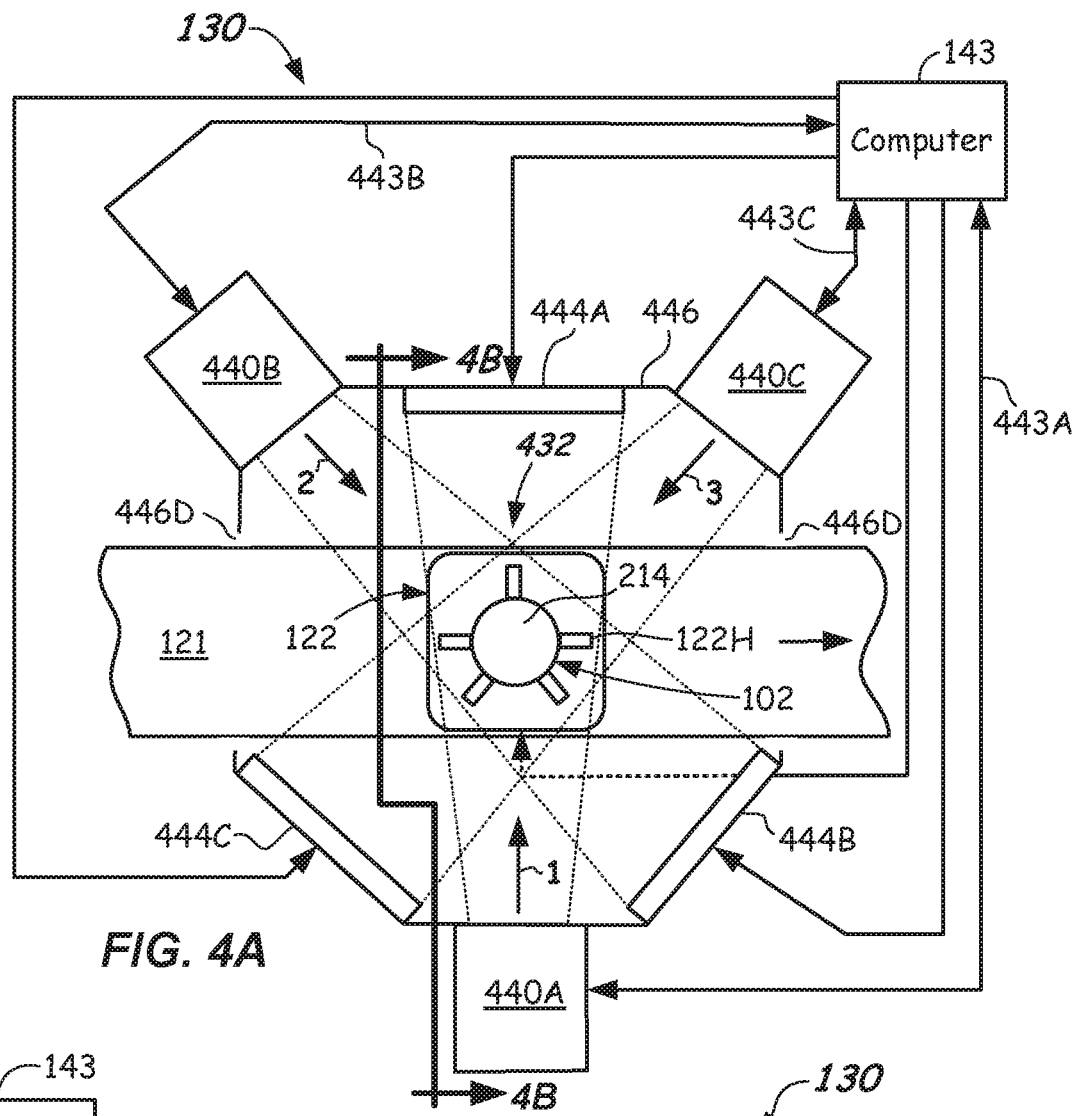
FIG. 4A illustrates a schematic top view of a quality check module (with ceiling removed) including multiple viewpoints and configured to capture and analyze multiple images to enable determining a presence of an interferent according to one or more embodiments.
Figure 4B:
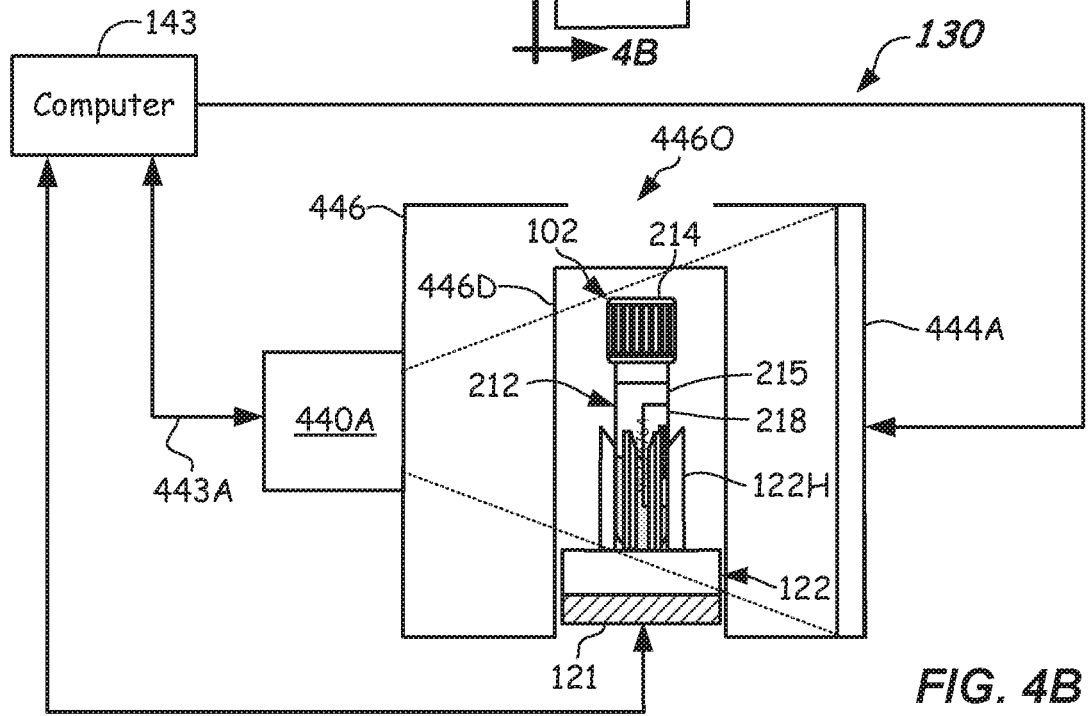
FIG. 4B illustrates a schematic side view of the quality check module (with front enclosure wall removed) of FIG. 4A taken along section line 4B-4B of FIG. 4A according to one or more embodiments.

Before explaining the rapid training method in detail, the configuration of the quality check module 130, which may also be used for training, will be described. As shown in FIGS. 4A-4B, the quality check module 130 configured to carry out the HILN characterization as well as the training methods are provided. Quality check module 130 may be configured to image the specimen 212 and adapted to pre-screen for a presence of an interferent (e.g., H, I, and/or L or N) in a specimen 212 (in the serum or plasma portion 212SP thereof) prior to analysis by the one or more analyzers 106, 108, 110.

Now referring to FIGS. 1, 4A, and 4B, a first embodiment of a quality check module 130 is shown including multiple image capture devices 440A-440C. Three image capture devices 440A-440C are shown and are preferred, but optionally a single image capture device, two or more, or four or more could be used. Image capture devices 440A-440C may be any suitable device for capturing well-defined digital images, such as conventional digital cameras capable of capturing a pixelated image, charged coupled devices (CCD), an array of photodetectors, one or more CMOS sensors, or the like. For example, the image capture devices 440A, 440B, 440C illustrated in FIG. 4A are configured to capture images from three different lateral viewpoints (viewpoints labeled 1, 2, and 3). For example, the captured image size may be about 2560×694 pixels, for example. In another embodiment, the image capture devices 440A, 440B, 440C may capture an image size that may be about 1280×387 pixels, for example. Other image sizes and pixel densities may be used.

Figures 3A, 3B:
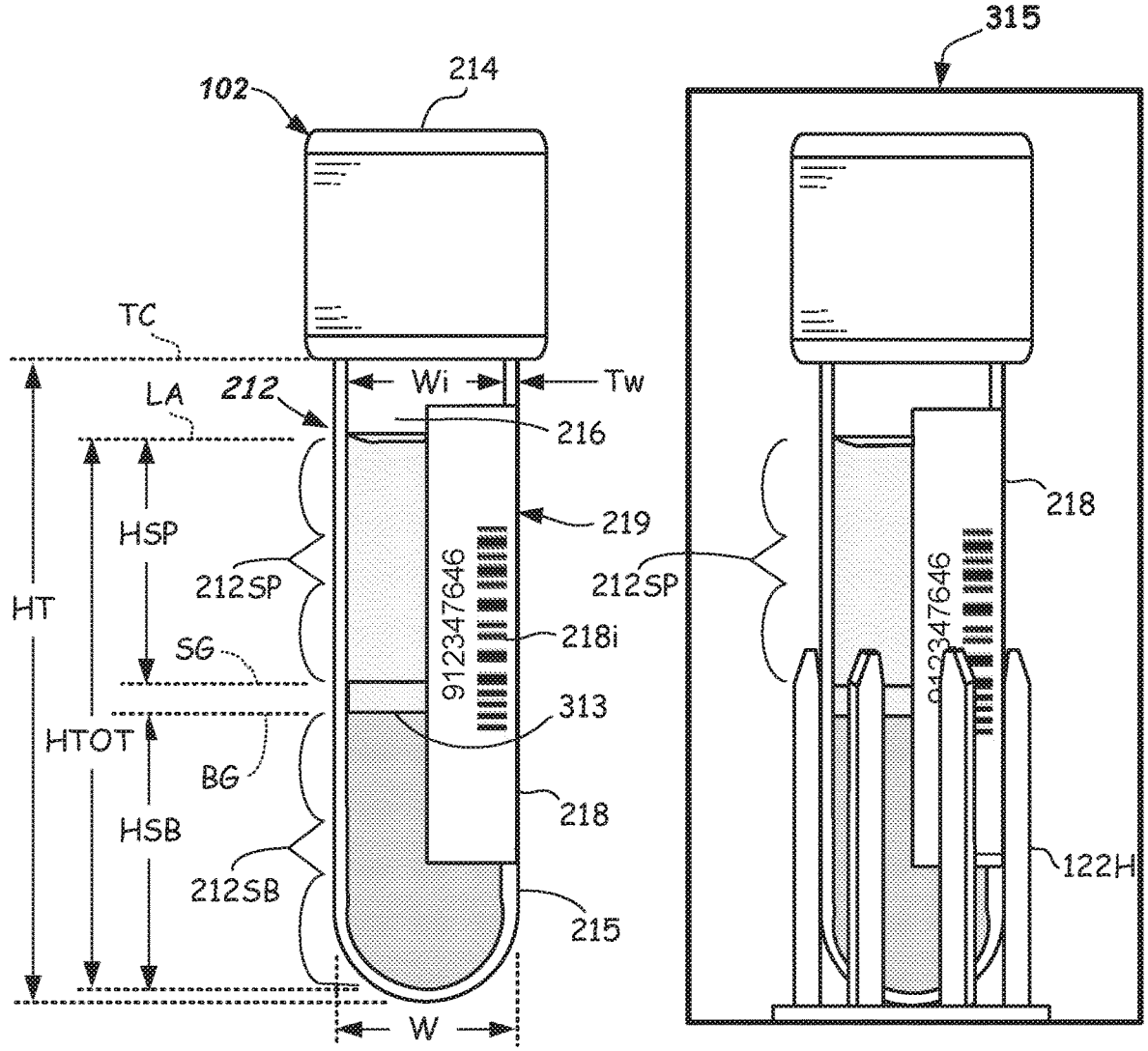
FIG. 3A illustrates a side view of a specimen container including a barcode label, a separated specimen including a serum or plasma portion containing an interferent, a settled blood portion, and a gel separator therein.
FIG. 3B illustrates a side view image of a specimen container including a barcode label, a specimen including a serum or plasma portion containing an interferent, a settled blood portion, and a gel separator, the specimen container being supported in an upright orientation in a holder and illustrating a rectangular imaging region.

Each of the image capture devices 440A, 440B, and 440C may be configured and operable to capture lateral images of at least a portion of the specimen container 102, and at least a portion of the specimen 212. For example, the image capture devices 440A-440C may capture an image 315, such as is shown in FIG. 3B, including part of the label 218 and part or all of the serum or plasma portion 212SP. For example, in some instances, part of a viewpoint 1-3 may be partially occluded by label 218. In some embodiments, one or more of the viewpoints 1-3 may be fully occluded, i.e., no clear view of the serum or plasma portion 212SP is possible. However, even in cases where a side (front side or back side) of a viewpoint 1-3 is fully occluded by one or more labels 218, the characterization method may still be able to distinguish the boundaries of the serum or plasma portion 212SP through the one or more occluding labels 218 upon being appropriately trained.

In the embodiment shown, the plurality of image capture devices 440A, 440B, 440C are configured to capture lateral images of the specimen container 102 and specimen 212 at an imaging location 432 from the multiple viewpoints 1-3. The viewpoints 1-3 may be spaced so that they are approximately equally spaced from one another, such as about 120° from one another, as shown. As depicted, the image capture devices 440A, 440B, 440C may be arranged around the track 121. Other arrangements of the image capture devices may be used. In this way, the images of the specimen 212 in the specimen container 102 may be taken while the specimen container 102 is residing in the carrier 122 at the imaging location 432. The field of view of the multiple images obtained by the image capture devices 440A, 440B, and 440C may overlap slightly in a circumferential extent.

In one or more embodiments, the carriers 122 may be stopped at a pre-determined location in the quality check module 130, such as at the imaging location 432, i.e., such as at a point where normal vectors from each of the image capture devices 440A, 440B, 440C intersect each other. A gate or the linear motor of the carrier 122 may be provided to stop the carriers 122 at the imaging location 432, so that multiple quality images may be captured thereat. Training images may be captured at the imaging location 432 during training. In an embodiment where there is a gate at the quality check module 130, one or more sensors (like sensors 116) may be used to determine the presence of a carrier 122 at the quality check module 130.

The image capture devices 440A, 440B, 440C may be provided in close proximity to and focused to capture an image window at the imaging location 432 having the size of the image 315, wherein the image window is an area including an expected location of the specimen container 102. Thus, the specimen container 102 may be stopped so that it is approximately located in a center of the image window, and thus at the center of the image 315, in some embodiments.

In operation of the quality check module 130, each training and testing image may be triggered and captured responsive to a triggering signal provided in communication lines 443A, 443B, 443C that may be sent by the computer 143. Each of the captured images may be processed by the computer 143. In one particularly effective method, high data rate (HDR) processing may be used to capture and process the image data from the captured images. In more detail, multiple images are captured of the specimen 212 at the quality check module 130 at multiple different exposures (e.g., at different exposure times) while being sequentially illuminated at one or more different spectra. For example, each image capture device 440A, 440B, 440C may take 4-8 images of the specimen container 102 including the serum or plasma portion 212SP at different exposure times at each of multiple spectra. For example, 4-8 images may be taken by image capture device 440A at viewpoint 1 while the specimen 212 is backlit illuminated with light source 444A that has a red spectrum. Each image may be at a different exposure. Additional like images may be taken sequentially at viewpoints 2 and 3, for example.

In some embodiments, the multiple spectral images may be accomplished using different light sources 444A-444C emitting different spectral illumination. The light sources 444A-444C may back light the specimen container 102 (as shown). The multiple different spectra light sources 444A-444C may be RGB light sources, such as LEDs emitting nominal wavelengths of 634 nm+/− 35 nm (Red), 537 nm+/− 35 nm (Green), and 455 nm+/− 35 nm (Blue). In other embodiments, the light sources 444A-444C may be white light sources. In cases where the label 218 obscures multiple viewpoints, IR backlighting or NIR backlighting may optionally be used. Furthermore, RGB light sources may be used in some instances even when label occlusion is present. In other embodiments, the light sources 444A-444C may emit one or more spectra having a nominal wavelength between about 700 nm and about 1200 nm.

In the way of a non-limiting example, to capture images at a first wavelength, three red light sources 444A-444C (wavelength of about 634 nm+/− 35 nm) may be used to sequentially illuminate the specimen 212 from three lateral locations. The red illumination by the light sources 444A-444C may occur as the multiple images (e.g., 4-8 images or more) at different exposure times are captured by each image capture device 440A-440O from each viewpoint 1-3. In some embodiments, the exposure times may be between about 0.1 ms and 256 ms. Other exposure times may be used. In some embodiments, each of the respective images for each image capture device 440A-440O may be taken sequentially, for example. Thus, for each viewpoint 1-3, a group of images are sequentially obtained that have red spectral backlit illumination and multiple (e.g., 4-8 exposures, such as at different exposure times). The images may be taken in a round robin fashion, for example, where all images from viewpoint 1 are taken followed sequentially by viewpoints 2 and 3 and stored in memory of the controller 143. This sequence may be accomplished for training images as well as for later testing images captured.

In each embodiment, the quality check module 130 may include a housing 446 that may at least partially surround or cover the track 121 to minimize outside lighting influences. The specimen container 102 may be located inside the housing 446 during the image-taking sequences. Housing 446 may include one or more doors 446D to allow the carriers 122 to enter into and/or exit from the housing 446. In some embodiments, the ceiling may include an opening 446O to allow a specimen container 102 to be loaded into the carrier 122 by a robot including moveable robot fingers from above.

Once the red illuminated images are captured in the embodiment of FIGS. 4A-4B, another spectra of light, for example, green spectral light sources 444A-444C may be sequentially turned on (nominal wavelength of about 537 nm with a bandwidth of about +/− 35 nm), and multiple images (e.g., 4-8 or more images) at different exposure times may be sequentially captured by each image capture device 440A, 440B, 440C. This may be repeated with blue spectral light sources 444A-4440 (nominal wavelength of about 455 nm with a bandwidth of about +/− 35 nm) for each image capture devices 440A, 440B, 440C. The different nominal wavelength spectral light sources 444A-444C may be accomplished by light panels including banks of different desired spectral light sources (e.g., R, G, B, W, IR, and/or NIR) that can be selectively turned on and off, for example. Other means for backlighting may be used.

The multiple images taken at multiple exposures (e.g., exposure times) for each respective wavelength spectra may be obtained in rapid succession, such that the entire collection of backlit images for the specimen container 102 and specimen 212 from multiple viewpoints 1-3 may be obtained in less than a few seconds, for example. In one example, 4 different exposure images for each wavelength at three viewpoints 1-3 using the image capture devices 440A, 440B, 440C and back lighting with RGB light sources 444A-444C will result in 4 images×3 spectra×3 image capture devices=36 images. In another example, 4 different exposure images for each wavelength at three viewpoints using the image capture devices 440A, 440B, 440C and back lighting with R, G, B, W, IR, and NIR light sources 444A-444C will result in 4 images×6 spectra×3 cameras=72 images. This sequence may be used for training and also for testing, as will be apparent.

According to embodiments of the characterization methods, the processing of the image data may involve a pre-processing step including, for example, selection of optimally-exposed pixels from the multiple captured images at the different exposure times at each wavelength spectrum and for each image capture device 440A-440C, so as to generate optimally-exposed image data for each spectrum and for each viewpoint 1-3. This is pre-processing step is referred to as "image consolidation" herein.

For each corresponding pixel (or patch), for each of the images from each image capture device 440A-440C, pixels (or patches) exhibiting optimal image intensity may be selected from each of the different exposure images for each viewpoint 1-3. In one embodiment, optimal image intensity may be pixels (or patches) that fall within a predetermined range of intensities (e.g., between 180-254 on a scale of 0-255), for example. In another embodiment, optimal image intensity may be between 16-254 on a scale of 0-255), for example. If more than one pixel (or patch) in the corresponding pixel (or patch) locations of two exposure images is determined to be optimally exposed, the higher of the two can be selected.

The selected pixels (or patches) exhibiting optimal image intensity may be normalized by their respective exposure times. The result is a plurality of normalized and consolidated spectral image data sets for the illumination spectra (e.g., R, G, B, white light, IR, and/or IR-depending on the combination used) and for each image capture device 440A-440C where all of the pixels (or patches) are optimally exposed (e.g., one image data set per spectrum) and normalized. In other words, for each viewpoint 1-3, the data pre-processing carried out by the computer 143 results in a plurality of optimally-exposed and normalized image data sets, one for each illumination spectra employed. Data sets obtained in the manner can be used for both training and testing (once the system is trained).

Figure 5A:
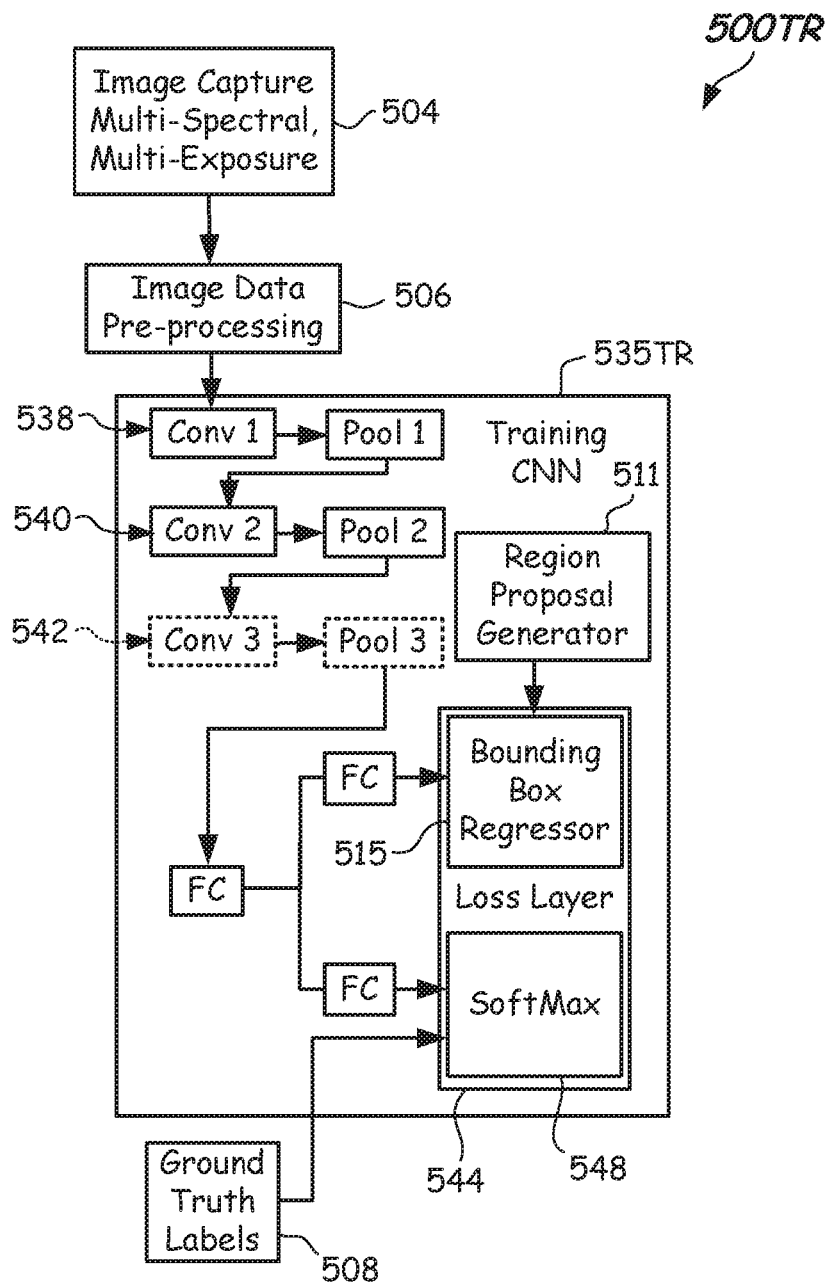
FIG. 5A illustrates a block diagram of an example architecture of a training CNN according to one or more embodiments.

Functional components of one embodiment of a training apparatus 500TR configured to carry out the training methods are shown in FIG. 5A. The training apparatus 500TR may be embodied as a quality check module 130 and configured as a training apparatus. As discussed above, the specimen container 102 including the specimen 212 is provided at the imaging location 432 (FIGS. 4A-4B) of the quality check module 130. Multiple training images can be captured of each specimen container type while containing training specimens 212. The training images are captured at the imaging location (e.g., at imaging location 432) or at a like location that includes a duplicate of the lighting conditions of the imaging location 432).

Multi-spectral, multi-exposure images are captured in 504 by one or more image capture devices (e.g., image capture devices 440A-440O or a subset thereof). The image data for each of the multi-spectral, multi-exposure images may be pre-processed in 506 as discussed above to provide a plurality of consolidated and optimally-exposed and normalized image data sets (hereinafter "image data sets"). During testing following the training method, similar generated image data sets from testing specimens 212 may be supplied as layers (as matrices) and input to a Testing CNN 535 (FIG. 5B) of a Testing CNN 500TE, which has been previously trained to recognize and categorize between HILN. As a result, a determination of HILN for a serum or plasma portion 212SP of any imaged specimen 212 may be provided.

During the training method (prior to testing), multiple sets of training specimens 212 are used to train the Training CNN 535TR. The Training CNN 535TR is trained according to the training method by imaging (e.g., with the quality check module 130 or a substantial duplicate thereof) a multitude of specimen containers 102 containing training specimen 212. The number of specimen images may include thousands (e.g., 5,000 or more, 10,000 or more, or even 15,000 or more). The images are obtained in 504 as discussed above and may include pre-processing of the image data in 506 to provide image consolidation and normalization. Ground truth labels 508 are provided as training input to the Training CNN 535TR along with the captured images from image capture 504 to establish corresponding HILN values (e.g., interferent type and/or HIL index gradations) for each training specimen 212. Size of the specimen container 102 may also be a training input.

In the depicted embodiments, the desired outcomes of the Testing CNN 535 (FIG. 5B) are n-Class Hemolytic, n-Class Icteric, n-Class Lipemic, and normal (N). Thus, the ground truth labels 508 as inputs will include HIL and n values across the expected range of values of HIL and N. HILN training values input as ground truth labels 508 have been predetermined for each training specimen 212 via separate HILN testing to provide an interferent type or N and if an interferent is present, possibly an index thereof. In the Testing CNN 535, the outputs of the Testing CNN 535 may be mapped to n set point values (where n is an integer value) for each of Hemolytic, Icteric, and Lipemic, and one for N normal. The value of n may be between 3 and 7, for example. However, other values of n may be used. For example, Testing CNN 535 outcomes may be assigned to a particular outcome based upon being within a certain pre-established range for each n (e.g., for n=3, then the range may be +/− 16.5%). Any suitable aggregation scheme may be employed for mapping to one of the available outputs of the Testing CNN 535.

Figures 3C, 3D:
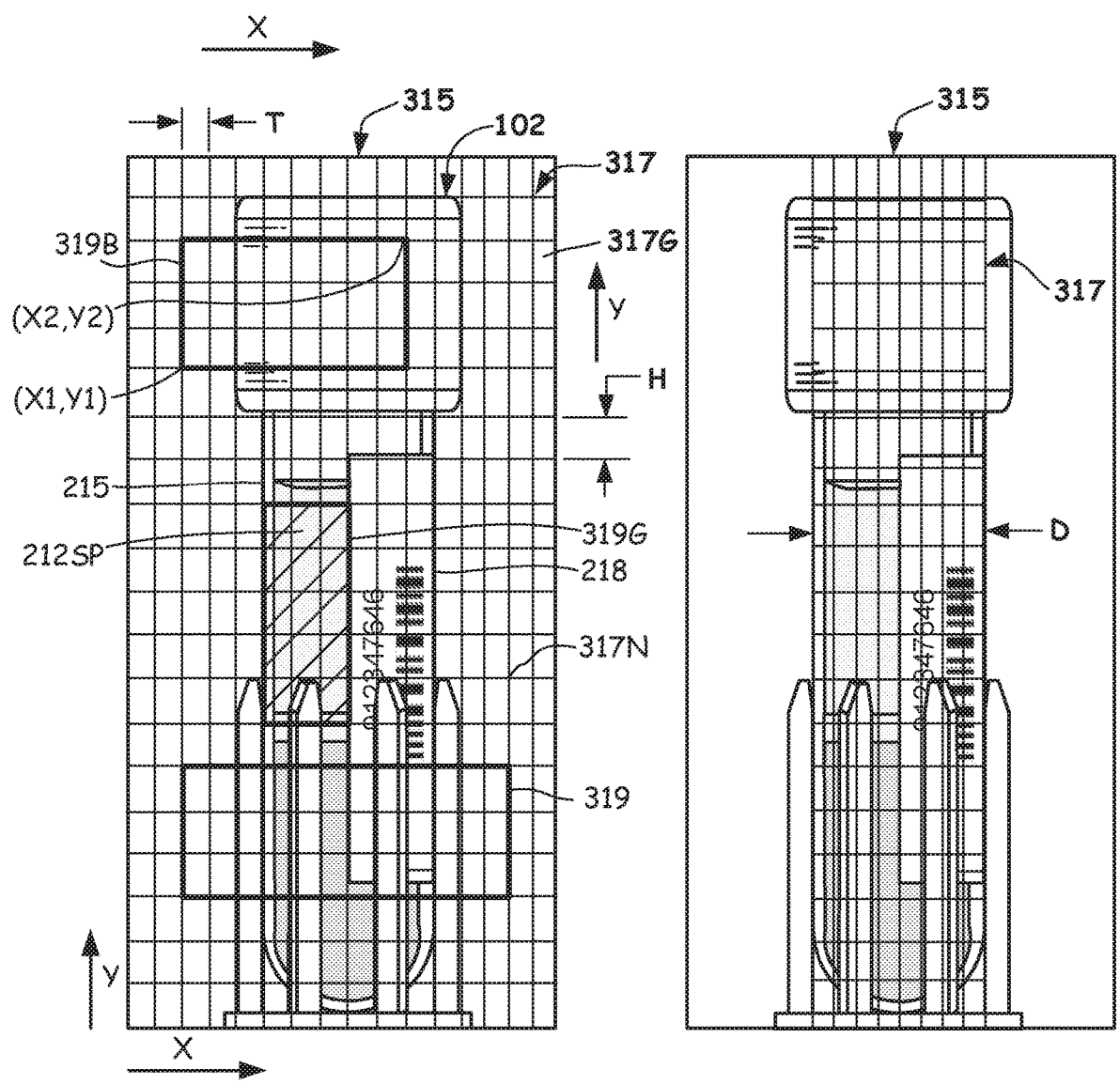
FIG. 3C illustrates a side view of the imaging region of FIG. 3B including an example superimposed grid according to one or more embodiments.
FIG. 3D illustrates a side view of the image of FIG. 3B with a simplified superimposed grid by having knowledge of the tube diameter according to one or more embodiments.

Again referring to FIG. 5A, the Training CNN 500TR may generate a region proposal 319 (FIG. 3C) with a region proposal generator 511. The region proposal 319 can be a randomly-generated region, which is a sub-region of the area of the image 315. The region proposal 319 is an attempt to provide an estimate of a region within the image 315 that corresponds in area and location to the serum or plasma portion 212SP of a training specimen 212. The region proposal 319 generated in region proposal generator 511 can be generated by and suitable means. In one embodiment, the region proposal 319 can be generated randomly by the region proposal generator 511. For example, a region proposal 319 may be generated by randomly selecting, via any suitable means, a sub-region (e.g., a rectangular box) from the virtual grid 317 that is superimposed over the image 315, as shown in FIG. 3C.

The virtual grid 317 may include a plurality of grid elements 317G of thickness T arranged along the X direction and height H arranged along the Y direction. The number of gradations of T in the X direction of the virtual grid 317 may be between about 10 to about 20 T units wide along a width of the specimen container 102, whereas the number of gradations of H in the Y direction can be between 20 to 40 units along a length/height of the specimen container 102, for example. Other numbers of grid elements 317G in the X and Y directions could be used. The gradations in X and Y should be fine enough so that a good representation of the area of the serum or plasma portions 212SP of each of the training specimens 212 can be found (e.g., a 90% matching area or higher). Referring to FIG. 3C, an example of a bad region proposal 319B is shown as a rectangular box in the upper left region of the image 315, whereas a good region proposal 319G is shown closely corresponding in location and size with the area of the serum or plasma portion 212SP. If enough random proposals are generated in 511, eventually, each of the training images 315 will be approximately matched with a suitably-close region proposal 319, i.e., approximately matching the area, location, and shape of the serum or plasma portion 212SP.

The region proposals may be generated by any suitable means. In some embodiments, diagonal corners of region proposals 319 may be generated by randomly selecting two nodes 317N within the virtual grid 317. The selected nodes are the diagonally-opposing corners of the region proposal 319. Any suitable selection scheme may be used for selecting the nodes/corners of the region proposal 319. For example, referring to the bad region proposal 319B, lower left node (X1, Y1) and upper right node (X2, Y2) can be randomly selected and define lower left and upper right corners of the region proposal 319 within the virtual grid 317. A plurality of such region proposals 319 (e.g., thousands) may be generated. Thus, region proposals 319 of various rectangular shapes (widths and heights) and locations within the virtual grid 317 will be generated and encompass a plurality of different sub-regions within the virtual grid 317. Some region proposals 319 will be a good fit (e.g., good region proposal 319G) with an area of a serum or plasma portion 212SP of a particular training specimen 212, while other will not be (e.g., bad region proposal 319B). Thousands of images 315 will be captured and processed and thousands of region proposals 319 will be generated by the region proposal generator 511.

As will be understood, the fit of the region proposals 319 will be tested/validated and the best of the region proposals 319 (e.g., a top 2,000 or more region proposals) will be selected that are the best fits ("matches") with the region of the serum or plasma portions 212SP of the training specimens 212. The region proposal generator 511 may, in some embodiments, be configured so that the same rectangular region proposal is never produced twice. Other means for selecting rectangular shapes of the region proposals 319 within the virtual grid 317 may be employed. For example, a center node 317N may be selected and then a random width and random height randomly selected to produce each region proposal 319.

Suitable smart convergence schemes may be used for guiding the region proposals 319 towards the relevant area of the serum or plasma portion 212SP. For example, various means may be used to reduce or limit the area within the virtual grid 317 in which the region proposals 319 will be generated, or otherwise reduce the size of the virtual grid 317. For example, as shown in FIG. 3D, having knowledge of the width W of the specimen container 102 can limit the size of the virtual grid 317 to only the region encompassing the width W. For example, the width W of the specimen container 102 may be provided as a ground truth label in 508.

The region proposal 319 is then provided as an input to the neural network (e.g., to the Training CNN 535) during training as shown in FIG. 5A. The generation of the region proposal 319 is automatic and does not require graphical input by the operator (e.g., graphical outline annotation) as was needed in the prior art.

In some embodiments, historical data on known sizes and locations of regions of serum or plasma 212SP may be used to further limit the starting size of the virtual grid 317 from which the region proposals 319 are generated from by the region proposal generator 511. Thousands of region proposals 319 of different sizes and locations are fed into the Training CNN 535 during training in addition to the thousands of training images 315. After input of a suitable number of images 315 and region proposals 319, the degree of convergence of the neural network (e.g., Training CNN 535) can be tested to determine if the region proposals 319 input thus far provide sufficient performance of the neural network (e.g., CNN 535), as discussed above.

In order to test/verify if a region proposal 317 is a good match with a serum or plasma portion 212SP of a training specimen 212, intensity gradients within the various region proposals 319 can be analyzed. For example, each grid element 317G in each of the training images 315 may include a plurality of rows and columns of pixels and each pixel may have an associated intensity value for each spectrum. Certain portions of the region proposal 317 may include grid elements 317G having relatively-high intensity gradients. Such intensity gradients may be an average intensity of the pixels (or patches within the specific grid elements 317G).

Each region proposal 319 may be tested/verified by filtering, such as by examining the light intensity gradients within each of the region proposals 319. For example, the degree of match may be discriminated by examining gradients of light intensity within only some regions of the training images 315. For example, gradients along a peripheral border of each region proposal 317 may first be quantified. Relatively high gradients within one or more sub-region of the region proposal 317 are indicative of a change of intensity that may be correlated to the presence of an interface, such as the liquid-air interface (LA), the serum blood interface (SB), or the serum-gel interface (SG), for example. Thus, the upper interface (LA) and/or the lower interface (SB) or the serum-gel interface (SG) may be discriminated based upon a change in intensity being identified within that sub-region and the ground truth labels 508 that was input with the images 315.

In some embodiments, the intensity gradients within individual grids elements 317G within the virtual grid 317 that are located along a periphery of the generated region proposals 319 (e.g., having a rectangular shape) may be quantified. These intensity gradient values (e.g., average intensity gradients) for each of the grid elements 317G located at the periphery of the region proposal 319 may be summed and/or summed and averaged for each region proposal 319. A large sum or average can mean there is a good correlation (e.g., good match) between an imaged serum or plasma portion 212SP and a region proposal 319. A relatively smaller sum or average can mean poor correlation (e.g., poor match). Thus, from the plurality of region proposals 319, a plurality of the best region proposals (e.g., several thousand of the best matching region proposals) may be selected based upon the degree of "match" with the inputted training images 315, i.e., those region proposals 319 that have the highest sums or averages are selected and the others can be discarded or not used.

For example, in the image 315, the liquid air interface LA is expected to be located between a certain range of rows of grids 317G (e.g., based on historical data) and the known size of the specimen container 102. Likewise, the serum blood interface SB is expected to be present between another range of rows of grids 317G (e.g., again based on historical data). In the case where a gel separator 313 is provided, the serum gel interface SG is expected to be present between yet another range of rows of grids 317G. Along the horizontal dimension, changes in intensity for a grid element 317G may mean that the edge of the tube 215 (the tube/air interface) is present, or that the edge of a label 218 is present. The Training CNN 535TR automatically determines region proposals 319 that may correspond to the serum or plasma portions 212P by verifying a bounding box hypothesis by using available gradient intensity information visible in the HDR imagery. Due to the characteristics of the various regions visible in the specimen 212, transitions between fluid regions (e.g., serum or plasma portions 212SP) and air 216 result in clear intensity gradients, which can be quantified and used to verify if a bounding box proposal captures the transitions. Regions such as settled blood portion 212SB, gel portion 313, or air 216 may be selected as part of the proposal generation during training, however the convergence of the learning process will not be fulfilled since the content is not discriminative enough to reduce the loss of the SoftMax classifier during training.

Changes in intensity within grid elements 317G in these areas can be indicative of such an interface or a side being present. The presence of an interface can be further confirmed by these intensity gradients being present within the grid 317 as a pattern, such as along a row or along a column of the grid 317. Intensity gradients may be determined by comparing average intensity values of the grid elements 317G along the periphery. To further limit to only viable regions, grid sub-regions of the virtual grid 317 identified as regions where serum or plasma portions 212SP may be present may be examined, while those grid elements 317G outside of the expected sub-regions may be ignored. For example, if the ground truth labels 508 included tube height HT, then areas that can only contain cap 214 or settled blood portion 212SB can be ignored and the region proposals 319 can be selected only from sub-regions of the grid 317 that do not include these areas. For example, a virtual mask or other virtual means for exempting certain regions of the grid 317 as being able to be selected may be used. In other embodiments, knowledge of the width W of the specimen container 102 as a ground truth label 508 can be used to reduce the size of the virtual grid 317. Thus, the convergence should be quicker due to less options for region proposals 319 being available to test/verify. The diameter and/or tube height input may be provided one time during the training method as a ground truth label 508 and then training using a large number of specimens of the same size can be undertaken before switching to another size. Thus, the diameter and/or height input need only be input as a ground truth label 508 when the size is changed.

Figure 5B:
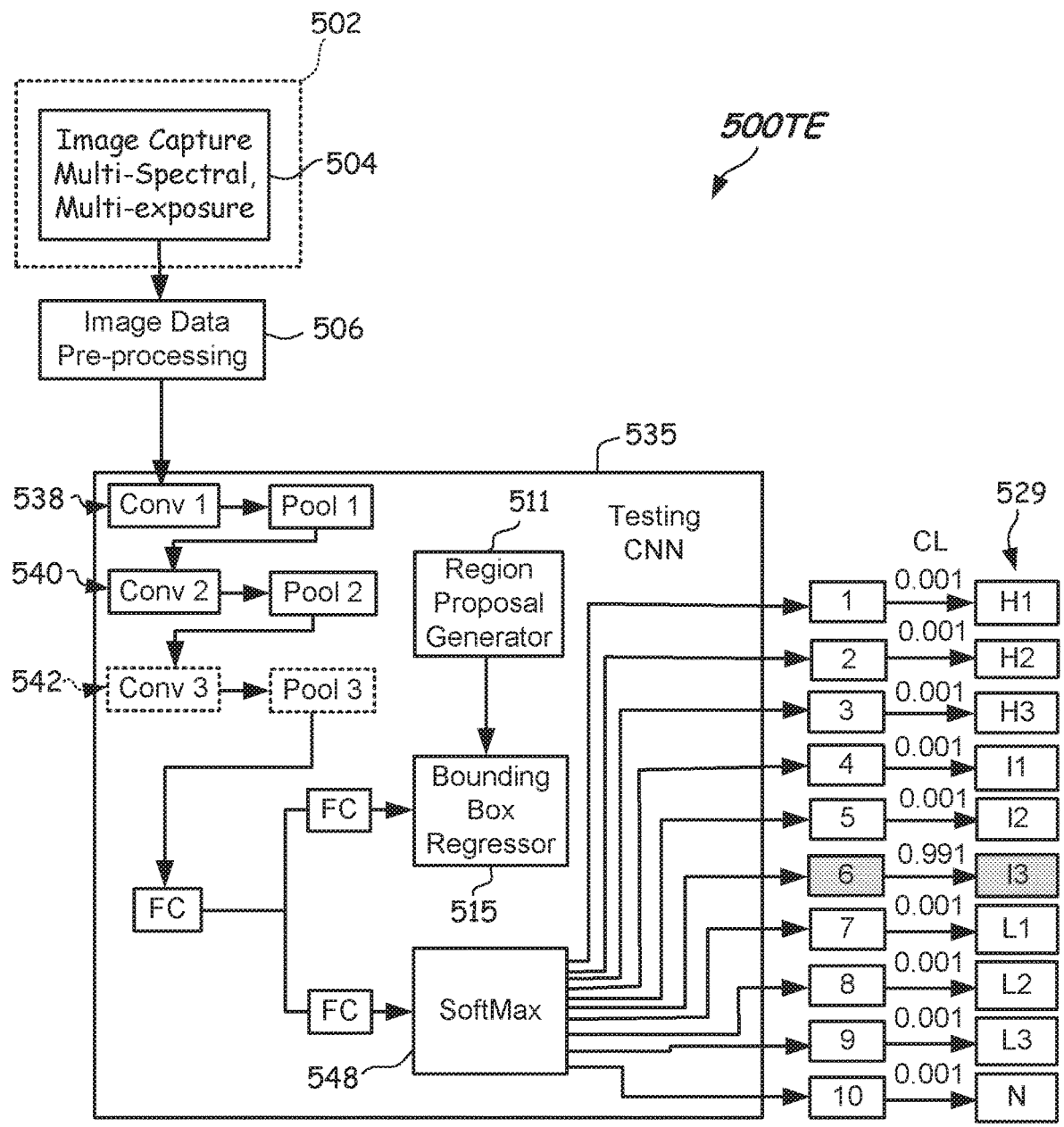
FIG. 5B illustrates a block diagram of an example architecture of a testing CNN according to one or more embodiments.

In the present embodiment of FIG. 5B, the outputs from the Testing CNN 535 at output 529 are n-classes of each of hemolytic (H1-H3), n-classes of Icteric (I1-I3) and, n-classes of lipemic (L1-L3). An output from the Testing CNN 535 as normal (N) at 529 is also available. As with training, during testing, a quality check module 130 can comprise an image capture device (e.g., 440A-440C) configured to capture multiple images of a specimen container 102 containing a serum or plasma portion 212SP of a test specimen 212. A computer 143 coupled to the image capture device can be configured and capable of being operated to input image data from the multiple images to a neural network (e.g., the Testing CNN 535 of FIG. 5B), and generate a region proposal of serum or plasma portion. The region proposal may be generated by the region proposal generator 511. The bounding box regressor 515 may function to converge the region proposal 319 to the actual size, shape, and location of the serum or plasma portion 212SP of the test specimen 212. The bounding box regressor 515 converges by comparing the inputted region proposal 319 geometrically to the response of the regressor 515 (output of the network). If a suitable area match is obtained, then the regressor 515 has converged. Area matches of greater than 80% could be considered a match, but even higher percentages (e.g., greater than 90%, greater than 95%, greater than 97%) can provide even more accurate results. The output from the neural network (Testing CNN 535) is a classification of the serum or plasma portion 212SP as being one or more of hemolytic, icteric, lipemic, and normal.

Each (pixel or patch) within the region proposal 319 generated by the region proposal generator 511 is processed by the Testing CNN 535 and has an output to one of HILN. These per pixel (or per patch) results may be mapped to an output channel (e.g., 1-10) and summed or aggregated by any suitable method and HILN determined based on which of the HILN has the highest count within the final region proposal.

In order to provide an improved final vote for HILN, in some embodiments post processing may be provided to traverse the counts from the other viewpoints (e.g., viewpoints 1-3). As such, a histogram over all the occurrences (counts) may be generated and an averaged HILN for the specimen 212 taking into account all the viewpoints may be generated.

In more detail, as before during training, during testing, multi-spectral, multi-exposure consolidated and normalized image data sets are input into the Testing CNN 535 as image data sets and are operated upon and processed by the Testing CNN 535. The output of the processing with the Testing CNN 535 may be multiple output possibilities (n-classes) for each of HIL or N, and of course for each viewpoint.

For the testing apparatus 500TE, per-channel confidence levels (CL) for HILN may be used, wherein each channel 1-10 is correlated with a particular class type (e.g., H1, H2, H3, I1, I2, I3, L1, L2, L3, and N) at 529. Thus, for each pixel (or patch) in the final region proposal (a matching proposal) determined by the bounding box regressor 515, an outputted class (H1-N) is provided. These per pixel (or per patch) outputs may be aggregated by any suitable post processing routine to sum up or otherwise process the results of each channel (e.g., channels 1-10 shown) and arrive at an overall determination of HILN from the available classes (e.g., H1, H2, H3, I1, I2, I3, L1, L2, L3, and N) at output 529. Any suitable voting scheme may be used, such as final pixel class=max CL, and then adding up the number of max CL for the serum or plasma portion 212SP. This same processing may be achieved per viewpoint. The classification results of the various viewpoints used may be summed or otherwise consolidated or averaged.

One example architecture of the Training CNN 535TR and Testing CNN 535 that can be used is shown in FIGS. 5A-5B. The CNNs described herein may be coded using any suitable scientific computing framework, program, or toolbox, such as, for example, Caffe available from Berkley Vision and Learning Center (BVLC), Theano, a Python framework for fast computation of mathematical expressions, TensorFlow, Torch, and the like.

In more detail, the CNNs 535TR, 535 may include a suitable number of operating layers to provide for deep learning. For example, the CNNs 535TR, 535 may comprise an architecture including at least two layers including convolution (Conv 1, Conv 2) and pooling (Pool 1 and Pool 2), and at least two additional fully-convolutional (FC) layers. In the depicted embodiment, two operating layers 538, 540 and one additional operating layer 542 can be provided. Fully-convolutional (FC) layers may be provided after the at least two operating layers 538, 540 and before each of the bounding box regressor 515 and the SoftMax 548. A loss layer 544 may be provided in the training CNN 535TR and may include the bounding box regressor 515 and a SoftMax 548. The described architecture of the CNNs 535TR, 535 may be used for finding a suitable region proposal 319 for each respective image. As will be recognized, the regressor 515 provides a potential bounding box annotation of the serum/plasma portion 212SP. During training, the bounding box proposal (region proposal 319) is provided to the regressor 515. A result is given by the network as a consequence of considering the image content. If the deviation between input to the regressor 515 and converged bounding box reaches a given minimum error (e.g., a suitably low geometric difference between the four corner points or % area match greater than some suitable percentage), that can be robustly calculated over a given set of input images (e.g. 10,000 training specimens 212), the regressor 515 can be assumed to be converged.

In the Testing CNN 535, once a suitable region proposal 319 is obtained, each layer of image data of that region proposal may scanned with a moving window approach to determine outputs at channels 1-10 and post-processed to aggregate an output at 529, which may be aggregated based on any suitable voting scheme. The moving window of input patch may be a 64×64 patch (64×64 pixels), for example. However, other sizes of patches may be used. Three major operating layers (Conv 1+Pool 1, Conv 2+Pool 2, and Conv 3+Pool 3) are shown, for example. The first layer 538 may extract very local structure edges; the second layer 540 can learn texture, which is a combination of edges; and the third layer 542 can form the parts. Each of the layers 538, 540, 542 of the CNNs 535, 535TR benefit from the multichannel input (e.g., multi-spectral, multi exposure information) which is processed. These operations over various input layers, and in particular three input layers (e.g., RGB), can be easily handled and represented by the deep learning network. This framework naturally integrates low, mid, and high level features, and leads to multilayer classification. The features (e.g., network with training weights) obtained from training CNN 535TR are stored in the computer 143 and can be used for later testing. Training may until suitable confidence in the Training CNN 535TR is achieved.

Again referring to FIGS. 5A and 5B, the CNNs 535TR, 535 can include a first layer 538 including a convolution layer (Conv 1), which may include 10 filters of size 5×5×12, for example. Other numbers of filters and filter sizes may be used. The resulting 10 feature maps are then fed to a max-pooling (Pool 1), which may take the max over 2×2 spatial neighborhoods with a stride of 1, separately for each channel. The purpose of this layer is to extract low-level features, especially like simple edges. This is followed by a the second layer 540 including a convolution layer (Conv 2) that may have 10 filters of size 5×5×20, and a max-pooling layer (Pool 2) which may take the max over 3×3 spatial neighborhoods with a stride of 2. The purpose of the second layer 540 is to learn different combination of simple edges to form texture. Thereafter, the resulting feature maps are fed into a third layer 542 including a convolution layer (Conv 3) that may have 20 filters of size 3×3×20, and a max-pooling layer (Pool 3), which may take the max over 2×2 spatial neighborhoods with a stride of 2 to learn combination of textures to form parts. Aforementioned max-pooling layers make the output of convolution networks more robust to local translations. Finally, the top layers are fully convolutional (FC) layers wherein each output unit is connected to all inputs. These layers are able to capture correlations between parts. The output of the last fully-convolutional layer (FC) is fed to an n-way SoftMax (where n=3 is the number of possible output classes) which produces a distribution over the n-class output channels. In short, the moving window of input patch, where each patch is classified with the trained CNN 535, gives a response towards one of the n-classes. The final region proposal found after regression by bounding box regressor 515 identifies the region to be classified. All regions outside of this region are ignored. Classification for the corresponding image data sets may be based on the majority voting results from these outputs. An additional step may be applied where per viewpoint results may be aggregated over the multiple viewpoints to obtain a confident decision, such as by averaging the results of the multiple viewpoints.

Figure 6A:
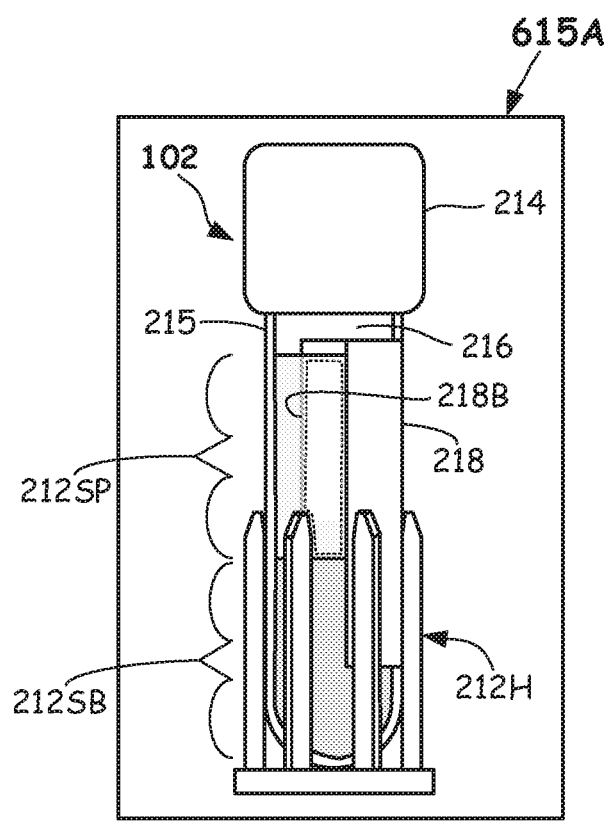
FIG. 6A illustrates a first image from a first viewpoint according to one or more embodiments.
Figure 6B:
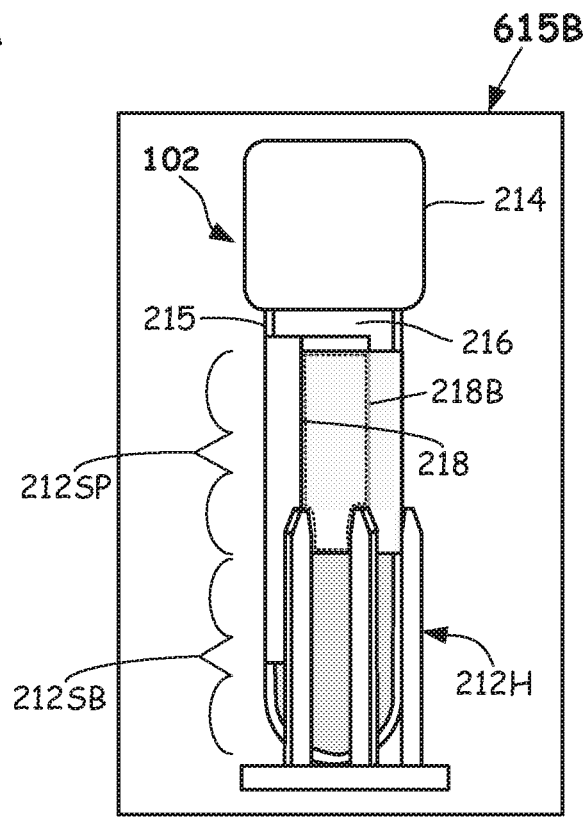
FIG. 6B illustrates a second image from a second viewpoint according to one or more embodiments.
Figure 6C:
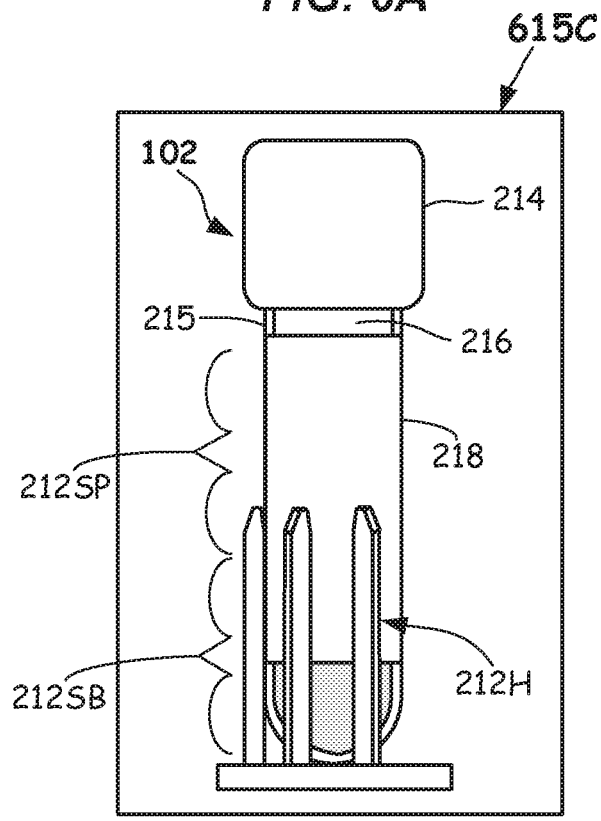
FIG. 6C illustrates a third image from a third viewpoint according to one or more embodiments.
Figure 6D:
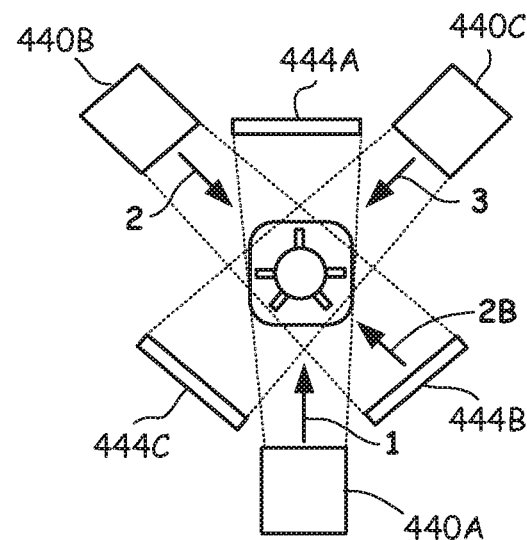
FIG. 6D illustrates a schematic top view illustrating the orientation of the various viewpoints according to one or more embodiments.

FIGS. 6A and 6B illustrate a front semantic image 615A, 615B from a first viewpoint 1, and second viewpoint 2 of image capture devices 440A, 440B (See FIG. 6D). In FIGS. 6A and 6B, some of the serum or plasma portion 212SP is occluded by label 218, and some of the backlight emitted from light sources 444A, 444B (FIG. 6D) is blocked by the back view label 218B (i.e., the portion of the serum or plasma portion 212SP that is occluded is shown dotted).

FIG. 6C illustrates a front semantic image 615C from viewpoint 3 of image capture device 440C (FIG. 6D). In FIG. 6C, all of the serum or plasma portion 212SP is occluded by label 218 from viewpoint 3. For each of these viewpoints 1, 2, 3, the Testing CNN 535 may output an HILN for the serum or plasma portion 212SP. Moreover, the characterization method may aggregate the results for each viewpoint 1, 2, 3 and provide an overall determination of HILN. In each case, the Testing CNN 535 takes into the serum or plasma portion 212SP that is visible but also the regions occluded by the back view label 218B.

Thus, the testing CNN 535TE outputs n-class output or N at 529. For example, if a majority of pixels (or patches) from the final region proposal are classified as N, then the serum or plasma portion 212SP may be categorized as being normal (N). If a majority of pixels (or patches) are classified as H, then the serum or plasma portion 212SP may be categorized as containing hemolysis (e.g., mapped to H1, H2, or H3). Likewise, if a majority of pixels (or patches) of the finally-determined region proposal are classified as I or L, then the serum or plasma portion 212SP may be categorized as Icterus (e.g., mapped to I1, I2, or I3), or Lipemia (e.g., mapped to L1, L2, or L3), respectively. In some embodiments, a weighted majority voting scheme may be also used to classify the specimen 212 using probabilities (CL) from the HILN results as a weight. Other means for characterizing the serum or plasma portion 212SP, as a whole, may be used.

Figure 7:
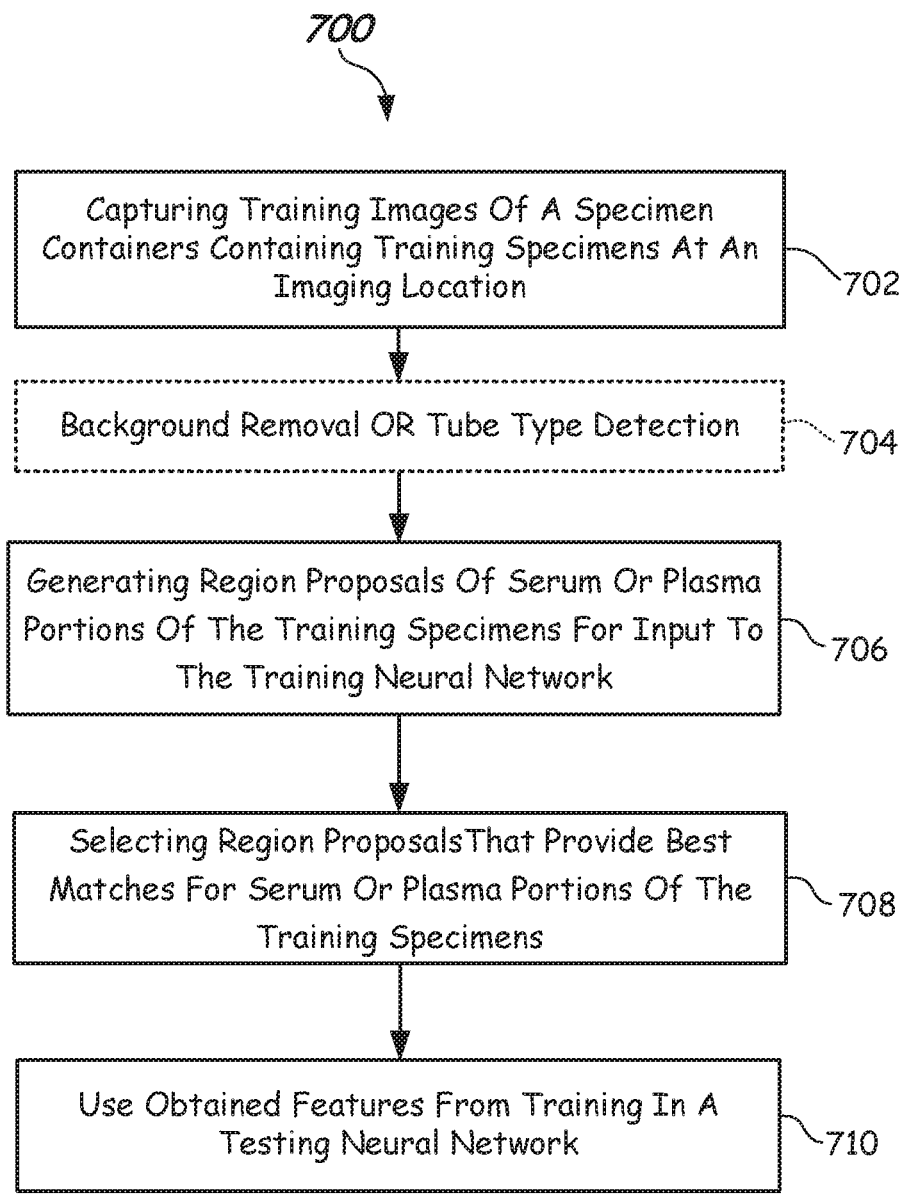
FIG. 7 is flowchart of a method of training a neural network according to one or more embodiments.

FIG. 7 illustrates a flowchart of a training method 700 according to embodiments of the disclosure. The training method 700 may be carried out by quality check module 130 (or a substantial duplicate thereof) and is operable to train a neural network (e.g., a Training CNN 535TR) as described herein. In particular, the training method 700 may be used to establish features of a testing neural network (e.g., Testing CNN 535) to determine a presence of an interferent (e.g., H, I, and/or L) or normality N of a serum or plasma portion 212SP of a specimen 212 according to one or more embodiments. Advantageously, the training method 700 does not require any manual graphical annotation (e.g., graphical outlining of the serum or plasma portion 212SP or other regions). The training method 700 includes, in 702, capturing training images of a specimen container (e.g., specimen container 102) including a training specimen (e.g., specimen 212) at an imaging location (e.g., imaging location 432). The training specimen 212 includes a serum or plasma portion (e.g., serum or plasma portion 212SP). The capturing multiple images may be from multiple viewpoints (e.g., viewpoints 1, 2, and 3). Moreover, the specimen container 102 may include one or more labels (e.g., label 218) thereon. Initial specimen containers 102 imaged may be devoid of labels 218 to help with training efficiency. The captured training images may be digital, pixelated images captured using one or more image capture devices (e.g., image capture devices 440A-440C).

The training method 700 further optionally includes, in 704, background removal or tube type detection. This image data pre-processing 506 may occur by capturing images of empty specimen containers 102 at the imaging location 432 under the various lighting and exposure conditions that are used for training the CNN and then subtracting those pixel intensity values to leave only the intensities corresponding to the specimen 212 and labels 218. Optionally, if the width W of the specimen container 102 is known from the ground truth label 508 input, then the width of the virtual grid 317 can be reduced. As was discussed above, the raw image data containing multi-spectral, multi-exposure images captured in 504 by the image capture devices 440A, 440B, 440C can also be consolidated and normalized in the image data pre-processing 506.

The training method 700 further includes, in 706, generating region proposals (e.g., region proposals 319) of a serum or plasma portion (e.g., serum or plasma portion 212SP) for input to the neural network (e.g., CNN 535TR). The image data (e.g., consolidated and normalized image data sets) from the multiple captured images (e.g., images 315) are submitted along with the region proposals 319 to the neural network (e.g., training CNN 535 TR) and processed thereby. The processing may be accomplished by the computer 143 described herein.

The training method 700 further includes, in 708, determining which ones of the region proposals (e.g., region proposals 319) provide a best match with the serum or plasma portions 212SP of the training specimens 212. Best match can be selected by taking the top percentage or number of the region proposals 319 based on peripheral intensity gradient data, as described above. However, other means for selecting the best matches may be used.

According to the method, once the training CNN 535TR is sufficiently trained in 710, then the obtained features (e.g., network and weights) from the training CNN 535TR may be used in the testing neural network (e.g., Testing CNN 535). Accordingly, based on the foregoing it should be apparent that an improved training method 700 is provided that provides ease of training of a neural network (e.g., CNN) by substantially eliminating manual graphical annotation input of the serum or plasma portion 212SP of training specimens 212.

Figure 8:
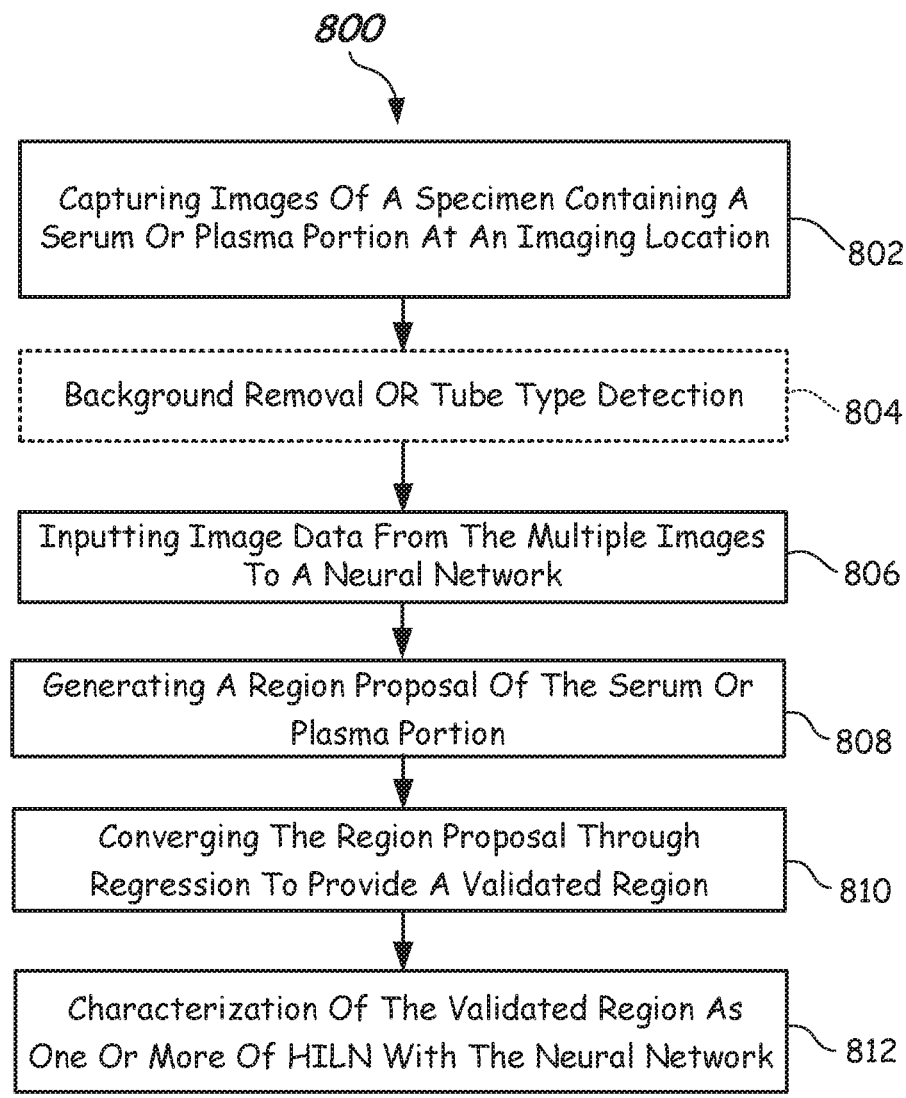
FIG. 8 is flowchart of a method of characterizing a specimen according to one or more embodiments.

FIG. 8 illustrates a flowchart of a testing method 800 according to embodiments of the disclosure. The testing method 800 may be carried out by quality check module 130 as described herein. In particular, the testing method 800 may determine a presence of an interferent in a specimen 212 according to one or more embodiments. The characterization method 800 includes, in 802, capturing multiple images of a specimen container (e.g., specimen container 102) containing a serum or plasma portion (e.g., serum or plasma portion 212SP) of a specimen (e.g., specimen 212). The capturing multiple images may be from multiple viewpoints (e.g., viewpoints 1, 2, and 3). Moreover, the specimen container 102 may include one or more labels (e.g., label 218) thereon. The one or more images may be digital, pixelated images captured using one or more image capture devices (e.g., image capture devices 440A-440C).

The characterization method 800 can optionally include, in 804, background removal or tube type detection as described herein. As will be apparent, this can allow the sub-region within the virtual grid 317 for selection of region proposals 319 to be area limited, as outlined herein. The characterization method 800 further includes, in 806, inputting image data (e.g., consolidated and normalized image data sets) from the multiple images to a neural network (e.g., convolutional neural network-Testing CNN 535).

The characterization method 800 further includes, in 808, generating a region proposal (e.g., region proposal 319) of the serum or plasma portion 212SP, and in 810 converging the region proposal 319 through regression to provide a validated region. The validated region is one that closely matches the size, shape, and location of the serum or plasma portion 212SP. Convergence is determined as discussed above (e.g., based on geometric measurements) wherein the input region proposal 319 from the region proposal generator 511 should sufficiently correspond to the output of the regressor 515 within a defined error corridor.

Finally, the method 800 includes characterization of the validated region and one or more HILN with the Convolutional Neural Network (e.g., Testing CNN 535) in 812. In particular, the characterization method 800 can output from the convolutional neural network (e.g., Testing CNN 535) a classification of the validated region corresponding to the serum or plasma portion 212SP as being one or more of hemolytic, icteric, lipemic, and normal (i.e., H, I, L, H and I, H and L, I and L, H, I, and L, or N).

The multiple images may include multiple images captured from each viewpoint at different exposure times and/or at different spectral illumination (e.g., R, G, B, white light, IR, and/or near IR). For example, there may be 4-8 different exposures or more taken at different exposure times for each viewpoint under the different spectral illumination conditions. Other numbers of exposures and spectral illumination may be used.

Accordingly, based on the foregoing it should be apparent that an improved characterization method 800 is provided that readily characterizes the serum or plasma portion 212SP by using a region proposal (e.g., region proposal 319). As should be apparent, the above characterization methods 800 may be carried out using a quality check module (e.g., quality check module 130), comprising a plurality of image capture devices (e.g., image capture devices) 440A-440C arranged around an imaging location (e.g., imaging location 432), and configured to capture multiple images from multiple viewpoints (e.g., multiple viewpoints 1-3) of a specimen container 102 including one or more labels 218 and containing a serum or plasma portion 212SP of a specimen 212, and a computer (e.g., computer 143) coupled to the plurality of image capture devices and adapted to process image data of the multiple images. The computer (e.g., computer 143) may be configured and capable of being operated to process the multiple images from the multiple viewpoints (e.g., viewpoints 1-3) to provide HILN determination.

Various selected components, features, or embodiments may be described individually herein. It should be noted that such components, features, or embodiments may be used in substitution with other individually-described components, features, or embodiments, or even in combination with other described components, features, or embodiments herein, as is practical. While the embodiments of the disclosure are susceptible to various modifications and alternative forms, specific apparatus, system, and methods have been shown by way of example in the drawings and are described in detail herein. It should be understood, however, that it is not intended to limit the disclosure to the particular apparatus, systems, and methods disclosed but, to the contrary, the intention is to cover all modifications, equivalents, and alternatives falling within the scope of the claims.

What is claimed is:

1. A method of training a neural network, comprising:
capturing training images of a specimen container containing training specimens at a imaging location;
generating region proposals of a serum or plasma portion for input to the neural network; and
selecting region proposals that provide best matches for serum or plasma portions of the training specimens.

2. The method of claim 1, wherein the region proposals comprise sub-regions of a virtual grid superimposed over the training images.

3. The method of claim 2, wherein the virtual grid comprises multiple grid elements of dimension of W in width×H in height.

4. The method of claim 2, wherein each of the region proposals comprises a rectangular sub-region within the virtual grid.

5. The method of claim 2, wherein the region proposals are randomly selected.

6. The method of claim 1, wherein the selecting region proposals comprises selecting a best 2,000 or more of the region proposals that are generated.

7. The method of claim 1, wherein the best matches for the serum or plasma portions of the training specimens are based upon intensity gradients within each of the region proposals.

8. The method of claim 1, wherein the best matches for the serum or plasma portions of the training specimens are based upon intensity gradients at the periphery of each of the region proposals.

9. The method of claim 1, wherein the best matches for the serum or plasma portions of the training specimens are based upon summing intensity gradients at the periphery of each of the region proposals.

10. The method of claim 1, wherein the convolutional neural network comprises an architecture including at least two layers configured to carry out convolution and pooling, and at least two additional fully-convolution layers.

11. The method of claim 1, wherein the convolutional neural network comprises an architecture including a loss layer with a bounding box regressor.

12. The method of claim 1, wherein the convolutional neural network comprises an architecture including a loss layer with a bounding box regressor and a SoftMax.

13. The method of claim 1, wherein the convolutional neural network comprises an architecture including at least three layers including convolution and pooling, and at least two fully-convolutional layers, and a loss layer with a bounding box regressor and a SoftMax.

14. The method of claim 1, wherein the capturing training images comprises different exposures for each of multiple spectra.

15. The method of claim 1, wherein the capturing training images comprises providing different exposure times for each spectrum of red, green, and blue.

16. The method of claim 1, wherein the capturing training images involves capturing images from multiple viewpoints with multi-spectral, multi-exposure images for each viewpoint.

17. A method of characterizing a specimen using a trained neural network, comprising:
capturing images of a specimen container containing the specimen at an imaging location;
generating a region proposal of a serum or plasma portion for input to the neural network; and
converging the region proposal to provide a match for the serum or plasma portion of the specimen through regression to provide a validated region.

18. The method of characterizing a specimen using a trained neural network of claim 17, comprising characterization of the validated region as containing one or more of hemolysis, Icterus, lipemia, or being normal with the trained neural network.

19. A quality check system, comprising:
an image capture device configured to capture multiple images of a specimen container containing a serum or plasma portion of a specimen; and
a computer coupled to the image capture device, the computer configured and capable of being operated to:
input image data from the multiple images to a neural network,
generate a region proposal of serum or plasma portion,
converge the region proposal through regression to provide a validated region, and
output from the neural network a classification of the validated region as being one or more of hemolytic, icteric, lipemic, and normal.

20. The quality check system of claim 19, wherein the neural network comprises an architecture including a bounding box regressor and a SoftMax.

21. The quality check system of claim 19, wherein the neural network comprises an architecture including at least three layers including convolution and pooling, at least two fully-convolutional layers, a bounding box regressor, and a SoftMax.

22. The quality check system of claim 19, wherein the multiple images are captured as multi-spectral, multi-exposure images.

23. The quality check system of claim 19, wherein the multiple images are captured from multiple viewpoints with multi-spectral, multi-exposure images for each viewpoint.

* * * * *